(12) United States Patent  
Ossart et al.

(10) Patent No.: US 7,930,110 B2
(45) Date of Patent: Apr. 19, 2011

(54) METHOD AND DEVICE FOR BIOMASS DETERMINATION IN A MEDIUM, IN PARTICULAR A MEDIUM CONTAINING BIOLOGICAL CELLS, AND MEASUREMENT APPARATUS IMPLEMENTING SAME

(75) Inventors: Frédéric Ossart, Langlade (FR); Charles Ghommidh, Saint Gely du Fesc (FR); Geoffrey Esteban, Nimes (FR)

(73) Assignee: Nanotec Solution, Nimes (FR)

( * ) Notice: Subject to any disclaimer, the term of this patent is extended or adjusted under 35 U.S.C. 154(b) by 248 days.

(21) Appl. No.: 11/660,447

(22) PCT Filed: Aug. 16, 2005

(86) PCT No.: PCT/FR2005/002091
§ 371 (c)(1),
(2), (4) Date: Jun. 26, 2008

(87) PCT Pub. No.: WO2006/021691
PCT Pub. Date: Mar. 2, 2006

(65) Prior Publication Data
US 2008/0262748 A1 Oct. 23, 2008

(30) Foreign Application Priority Data
Aug. 16, 2004 (FR) .................................. 04 08907

(51) Int. Cl.
*G01N 27/22* (2006.01)
(52) U.S. Cl. .............................. 702/21; 702/22; 324/684
(58) Field of Classification Search .................... 702/22, 702/23, 25, 252, 64, 75, 85; 324/658, 674, 324/684
See application file for complete search history.

(56) References Cited

U.S. PATENT DOCUMENTS

| 4,214,203 | A |   | 7/1980  | Coster et al. |
|-----------|---|---|---------|---------------|
| 4,810,650 | A | * | 3/1989  | Kell et al. ................... 435/287.1 |
| 4,965,206 | A |   | 10/1990 | Kell |
| 5,551,281 | A |   | 9/1996  | Todd |
| 6,496,020 | B1| * | 12/2002 | Davey et al. .................. 324/674 |

FOREIGN PATENT DOCUMENTS

EP 0 281 602 9/1988
(Continued)

OTHER PUBLICATIONS

Yardley, J.E., et al., "Correction of the Influence of Baseline Artefacts and Electrode Polarisation on Dielectric Spectra", Bioelectrochemistry, 2000, vol. 51, Elsevier, Document A.
Biomass Monitor 'Model 214M' User Manual, Jan. 26, 1998, Document B.

(Continued)

*Primary Examiner* — Manuel L Barbee
(74) *Attorney, Agent, or Firm* — Young & Thompson

(57) ABSTRACT

Method for biomass determination in a medium, in particular a medium containing biological cells suspended in a conductive fluid, the biomass concentration (X) being obtained from a difference between a first capacitance signal (C'1) of the medium, measured at a first frequency, and a second capacitance signal (C'2) of the medium, measured at a second frequency. The method includes a separate correction of each of the measured signals, based at least on one correction level, the first correction level including a correction of the signals measured in accordance with a model dependent on the conductance of the medium at the first and second frequencies. The invention is useful in biomass measurement systems.

57 Claims, 5 Drawing Sheets

FOREIGN PATENT DOCUMENTS

| | | |
|---|---|---|
| EP | 0 282 532 | 9/1988 |
| EP | 0 620 919 | 10/1994 |
| EP | 1 085 316 | 3/2001 |
| EP | 1 138 758 | 10/2001 |
| FR | 2 812 725 | 2/2002 |
| FR | 2 835 921 | 8/2003 |
| WO | WO 88/02114 | 3/1988 |
| WO | WO 88/02115 | 3/1988 |
| WO | WO 93/14402 | 7/1993 |

OTHER PUBLICATIONS

Biomass Monitor 'Model 214A' User Manual, Mar. 11, 1994, Document C.

Carvell, J.P., "On-Line Biomass Monitoring with Scanning Radio-Frequency Impedance Spectroscopy", World Class Brewing Congress 2004, Jul. 24-28, 2004, Document D.

EPO Notification of 3rd Party Observation dated Nov. 12, 2010 from EP05798517.8.

* cited by examiner

METHOD AND DEVICE FOR BIOMASS DETERMINATION IN A MEDIUM, IN PARTICULAR A MEDIUM CONTAINING BIOLOGICAL CELLS, AND MEASUREMENT APPARATUS IMPLEMENTING SAME

BACKGROUND OF THE INVENTION

1. Field of the Invention

This invention relates to a method for the determination of biomass in a medium, in particular a medium containing biological cells. It also relates to a device for the implementation of this method, as well as a measurement device implementing this method, which can be used for a biomass measurement.

This is a method for determining dielectric characteristics, which on the one hand makes it possible to correct the main sources of errors encountered in the impedance measurements used for conductive media, and on the other hand to obtain parameters characterizing the β dispersion of biological cell suspensions.

2. Description of the Related Art

Measurements of electrical impedance, and in particular of dielectric permittivity, can be used in order to obtain in non-destructive manner information on the composition or structure of the media studied. Measurement of the biomass concentration in fermentation media is one example of the application of this technique. This measurement, which has now become practically a routine measurement, has resulted from a two-phase development.

A first phase, up to the end of the 1970s, made it possible for scientists to study the electrical properties of biological media and cell suspensions, and to show the relationship between cell concentration and dielectric permittivity. It is known from the work of researchers such as for example Fricke (1953, "Relation of the permittivity of biological cell suspensions to fractional cell volume" which appeared in Nature, 172, 4381, 731-732) and Schwann, (1957, "Electrical properties of tissues and cell suspensions" which appeared in Adv. Biol. Med. Phys., 5, 147-209), that a strong correlation exists between permittivity, measured in the radio frequency range and volume fraction of cells (yeasts, red blood cells etc.) in the medium studied. In fact, when a living cell is subjected to an electric field, the displacement of the ions inside the cell is limited by the cytoplasmic membrane, which induces a polarization phenomenon. Each cell then behaves like a small capacitor. The amplitude of this polarization, which can be evaluated by measuring the dielectric permittivity (or capacitance) of the medium, depends on the frequency of the electric field applied. At relatively high frequencies, of the order of 10 MHz and above, polarization is weak. The dielectric permittivity (and the capacitance) then substantially corresponds to that of medium devoid of cells. In contrast, at relatively low frequencies, of the order of 0.1 MHz, the cells are completely polarized, and the dielectric permittivity (and the capacitance of the suspension) is higher. This phenomenon, which therefore relates to measurements carried out in the so-called "radio" frequency range, is described in the scientific literature under the name of B dispersion. The form of this dispersion is characteristic, as illustrated by FIG. 1, the permittivity progressively reducing from a low frequency plateau to a high frequency plateau, following a reversed S-shaped curve. The mathematical relationship between biovolume and dielectric permittivity has been established. For spherical cells, the dielectric increment $\Delta\varepsilon$, established by finding the difference between the permittivity $e_l$ measured at low frequency and that $e_h$ measured at higher frequency, is proportional to the product P·r·Cm, an expression in which P is the volume fraction occupied by the biomass, r is the radius of the cells, assumed to be spherical, and Cm is the membrane capacitance, according to the relationship $$\Delta\varepsilon = \frac{9PrC_m}{4e_0},$$

As the cell volume is almost proportional to the cell mass, it is thus possible, by means of two measurements carried out at two frequencies on either side of the B dispersion range, to simply evaluate the concentration of microorganisms (bacteria, yeasts, animal cells etc.) in a culture medium.

Siugura et al., in the article "Dielectric behavior of yeast cells in suspension", which appeared in J. Gen. App. Microbiol., 10, 2, 163-174 (1964), have thus presented without ambiguity the linear experimental relationship between the dielectric increment, measured in a frequency range corresponding explicitly to the B dispersion, and the volume fraction of suspensions of *Saccharomyces*.

Up to the end of the 1970s, published works were most often concerned only with the study of "model" suspensions of cells in "ideal" media, water or saline solutions at low concentrations. In fact, the measurements, which most often used capacitance bridges with manual adjustment and platinated platinum electrodes, were tedious and difficult, thus preventing any practical development outside research laboratories. As discussed below, one of the main difficulties encountered by the experimenters was the polarization of the surface of the electrodes, which is capable of significantly disrupting the capacitance measurements. In spite of this, Gencer and Mutharasan, in the article "Determination of biomass concentration by capacitance measurement" which appeared in 1979 in the journal Biotechnol. Bioeng., 21, 6, 1097-1103, showed the benefit of capacitance measurements used for monitoring fermentations in situ and in real time.

The second phase commenced at the end of the 1970s, thanks to progress in electronics and the development of automated devices, in particular by Hewlett-Packard, which then radically changed the situation by simplifying the implementation of capacitance measurements, thus allowing their popularization. (T. Ichino (HP) and H. Ohkawara (HP) and N. Sugihara (HP). Vector impedance analysis to 1000 MHz. Hewlett-Packard Journal: technical information from the laboratories of Hewlett-Packard Company, 31 (1), pp. 22-31, January 1980; Y. Narimatsu (HP) and K. Yagi (HP) and T. Shimizu (HP). A versatile low-frequency impedance analyzer with an integral tracking gain-phase meter. Hewlett-Packard Journal: technical information from the laboratories of Hewlett-Packard Company, 32 (9), pp. 22-28, September 1981).

Clarke et al., in the article "Sensors for bioreactor monitoring and control—a perspective", published in J. Biotechnol, 1, 135-158, were among the first to explicitly mention the benefit of the technique for determining biomass concentration in fermentation, and propose a device making it possible, starting with a permittivity measurement, to monitor the growth of microbial cultures.

EP0282532 describes a method for measuring biomass which makes it possible, starting with a capacitance measurement carried out at a single frequency, chosen from the low-frequency range of the B dispersion, to obtain a signal representative of the biovolume. This method makes it possible to avoid measurements at multiple frequencies, which are necessary for estimating the amplitude of the β dispersion.

On the other hand, as indicated by the inventor himself (Yardley, Kell et al., 2000. On-line, real-time measurements of cellular biomass using dielectric spectroscopy, published in Biotechnology & Genetic Engineering Reviews, vol. 17, 2000, Pages 3-35), it is necessary to have a reference measurement obtained before the start of fermentation, in order to be able to evaluate the capacitance variation. The main drawback of this method is therefore its sensitivity to the errors linked to parasitic capacitance variations, as a function of time, frequency and conductivity of the medium, due to the polarization of the electrodes or to different imperfections in the materials used.

EP0281602, filed jointly with the preceding patent, presents a device for measuring the capacitance of a fermentation medium, which uses a technique for measuring the amplitude of the in-quadrature and in-phase demodulated signal;

EP0620919 describes a method for measuring gas hold-up with a device operating according to the principles described in the patent EP0281602, which uses two intensity measurements of the reactive current at a high frequency, one carried out before fermentation, the other during fermentation, the result being used to correct the biomass measurement;

If the measurement principle is simple, its implementation is rendered complex because of the influence of several variables, which act not only on the amplitude of the dielectric increment, but also on the general shape of the β dispersion curve. The expression generally adopted to describe this dispersion is the following $$\varepsilon = \varepsilon_h + \frac{\Delta\varepsilon 1 + \frac{f^{1-\alpha}}{f_c}\sin\alpha\frac{\pi}{2}}{1 + \frac{f^{2(1-\alpha)}}{f_c} + 2\frac{f^{1-\alpha}}{f_c}\sin\alpha\frac{\pi}{2}}$$

The point of inflexion of this curve, situated at mid-height between the two plateaux, corresponds to a frequency known as the characteristic frequency fc, as illustrated by FIG. 1. The gradient of the tangent at the point of inflexion depends on the superposition of several dispersions, of adjacent characteristic frequencies, induced for example by a variation in the size of the cells around an average value. The coefficient a, which makes it possible to take this phenomenon into account, is an empirical parameter known by the name Cole-Cole a dispersion factor.

The article by Yardley et al. (previously cited) examines all of the problems posed by the measurement. For example, the technical constraints mean that the measurements can generally be carried out neither at a sufficiently low frequency, nor at a sufficiently high frequency, which means that the plateaux on either side of the B dispersion zone cannot be reached. The dielectric increment cannot therefore be measured in its totality. The frequency characteristic fc is displaced under the influence of variations in the conductivity of the medium s m and the intracellular conductivity s c, the cell size r and membrane capacitance Cm, according to the relationship $$f_c = \frac{1}{2\pi r C_m \frac{1}{\sigma_c} + \frac{1}{2\sigma_m}}$$

which leads to variations in the capacitance measurement if the measurements cannot be carried out on the plateaux.

Finally, the gradient of the dispersion curve, around the characteristic frequency fc, is itself variable, as a function of the value of the a dispersion factor, which can induce variations in the measured capacitance, independent of variations in the cell concentration.

It is thus desirable to evaluate the dielectric (or capacitive) increment starting with measurements carried out at several frequencies, in order to reconstitute, optionally by extrapolating, the whole of the β dispersion curve. Impedance spectroscopy is then considered. Because of the form of the mathematical function describing the β dispersion, obtaining mathematical descriptors of the dispersion curve (Δ∈, fc, a) generally requires the implementation of so-called "non-linear" mathematical adjustment techniques, one of the best known being the Levenberg-Marquard iterative method.

These techniques are costly in terms of computing power (or time). Moreover, it is generally necessary to provide a starting value at different parameters in order that the iterative method converges towards a suitable solution. These techniques cannot therefore be implemented economically in microcontroller-based measurement systems, as encountered in numerous commercial measurement devices.

To these difficulties is added that linked to electrode surface polarization. In fact, in the impedance measurement systems using electrodes in direct contact with the medium, the measurement of the characteristics specific to the medium is disturbed in particular by the accumulation of charges at the surface of the electrodes, which causes a systematic polarization phenomenon. The capacitance which results from this is added to that of the medium and develops with the ionic conductivity of the medium. A second source of error is linked to the adsorption of compounds in solution on the electrodes. This adsorption causes a modification of the electric properties of the metal-liquid medium interface, which depending on the type of molecules adsorbed, results in a variation in capacitance, the direction and amplitude of which cannot be foreseen, and which we shall call random polarization. In practice, the amplitude of random polarization is clearly smaller than that of systematic polarization.

These problems are well known, and several methods have been proposed, in particular by Schwan in 1963 in his article "Determination of biological impedances", published in "Physical techniques in Biological research", vol 6, Nastuk ed., Academic Press, pp. 323-407, either to limit the polarization amplitude (modification of the state of the surface of the electrodes, systems with 4 electrodes, liquid electrodes), or to evaluate the polarization amplitude (variation in the inter-electrode distance), or to evaluate and correct, by calculation, the contribution of polarization of the electrodes. Theoretically, this last operation is possible because polarization of the surface of the electrodes diminishes rapidly with the measurement frequency. By carrying out a few measurements at low frequencies, it is possible to evaluate the polarization capacitance at higher frequencies, providing that its law of variation with frequency is known. A law of the type $$C_{pol} = C_{0pol} f^{-k}$$

is generally used, in which k is an experimental coefficient generally comprised between 1 and 2. It is then possible to correct the capacitance measurements by subtracting from them this estimation of the polarization capacitance.

Thus, Sugiura et al. describe, in the article "Dielectric behavior of yeast cells in suspension", J. Gen. App. Microbiol., 10, 2, 163-174 (1964), a correction of the capacitance measured in a suspension of yeasts, in which measurements carried out at low frequency were used in order to correct those carried out at higher frequencies.

Bordi et al. have proposed, in the article "Reduction of the contribution of polarization effects in the radiowave dielectric measurements of highly conductive biological cell suspension", Bioelectrochemistry 2001, a global non-linear adjustment method which allows the contribution of the capacitance of the electrodes to be eliminated.

The document EP0282532 (Kell) discloses an equivalent method, referred to as method 2f, which uses the relationship of the capacitance measurements carried out at two frequencies in the low part of the β dispersion, a frequency range where the influence of the polarization of the electrodes is predominant compared with that of the capacitance of the cell suspension. The drawback of this last method is that it explicitly assumes that the polarization of the electrodes follows a single fixed law, independent of the conductivity of the medium, and above all that it does not take into account the errors due to imperfections in the materials used.

Background to the Problem

From 1993, the Fogale company have undertaken the development of a measurement system with the purpose of resolving the main problems posed by capacitance measurements in fermentation. The main objective was the development of a system capable of carrying out measurements of biomass concentration in media with high electric conductivity, for example greater than 50 mS/cm, which is encountered under industrial fermentation conditions. This is the case when the culture media are prepared from beet molasses, or when organic acids are excreted by the microorganisms cultured, as during lactic, citric or gluconic fermentation. A second objective was to arrive at sensor geometry allowing use not only in an industrial medium, but also in the laboratory. It was thus necessary for the measurement probe to have a small diameter, in order to be suitable for standard 12 mm ports, encountered on all small fermenters, which in practice prevented the implantation of active circuits in the measurement probe, in the immediate vicinity of the electrodes, as practiced in other systems. The patent FR2812725 thus describes a device making it possible to achieve these objectives, and to design very long measurement probes. The patent FR2835921 describes an application for measuring the biomass of lactic bacteria in a highly conductive medium.

More specifically, a biomass measurement device such as that described in the document FR2812725 presents extremely high line effects, which are added to the capacitance linked to polarization of the surface of electrodes. The overall capacitive error can reach 150 pF/cm, which is much greater than the values corresponding specifically to the biomass present in the fermentation media (typically 0.1 to 10 pF/cm).

The in-line polarization correction methods mentioned previously do not take account of these electronic effects as the inventors of these methods used devices designed in accordance with good engineering practice, i.e. provided with electronics as close as possible to the electrodes (a few mm) in order to minimize the line effects. In order to be able to use a biomass measurement device such as that described in the document FR2812725, it is therefore necessary to correct not only the effects of systematic and random polarizations of the electrode surface of electrodes, but also the effects of the other sources of error.

SUMMARY OF THE INVENTION

The purpose of this invention is to propose a method for the determination of biomass in a medium, in particular a medium comprising cells in suspension in a fluid, which provides an effective correction of the errors observed in existing measuring devices.

This objective is achieved with a method for the determination of biomass, obtained from a difference between a first capacitance signal (C'1) of said medium, measured at a first frequency, and a second capacitance signal (C'2) of said medium, measured at a second frequency.

According to the invention, the method comprises a correction separate from each of the measured signals, according to at least one level of correction, this first level of correction comprising a correction of said measured signals according to a model dependent on the conductance of the medium at said first and second frequencies.

The determination method according to the invention can moreover advantageously comprise a second level of correction comprising a correction of said first and second corrected capacitance signals, starting from a third capacitance measurement carried out at a third frequency, itself corrected by a conductance measurement carried out at said third frequency.

When it is implemented for a medium comprising cells in suspension in a medium, the determination method according to the invention also comprises a third level of correction using a model of the behaviour of the β dispersion in said medium.

In the method according to the invention, the capacitance errors due to random polarization are corrected separately from those due to systematic polarization and those due to the electronics, and in that it also comprises:

global modelling of the systematic polarization and of the capacitance errors due to the overall errors of the electronics, in the form of a common equation $C_{cal}(G,f)$, a function of the conductance of the medium and of the excitation frequency of the conductive electrodes, such that this equation makes it possible to also eliminate the product of the combined effect of systematic polarization and of the overall errors of the electronics within the device, and, determination of a corrected capacitance value Cm_cor(G, f), by comparing each raw capacitance measurement Cm(G, f) originating from the device and carried out at a predetermined frequency, with the value of said common equation of the model $C_{cal}(G,f)$ at said predetermined frequency.

This method was designed to be used in line on a biomass measurement device as disclosed in the document FR2812725 in the name of the present applicant, but it can however be applied for any impedance measurement instrument using a sensor equipped with conductive electrodes immersed in a dielectric medium.

The method according to the invention also corrects the capacitive errors of the electronics, the capacitive errors of the line effects of the sensor, and the capacitive errors of the sensor (the inductive effects inter alia).

The common equation of the model $C_{cal}(G, f)$ can be in polynomial form, for example of order 3 or 4, and have coefficients calculated for a plurality of predetermined frequencies used by the device, or can be approximated by a polynomial.

The capacitance errors corrected by the common equation of the model $C_{cal}(G, f)$ can comprise capacitive errors as a function of the conductance and frequency.

The capacitance errors corrected by the common equation of the model $C_{cal}(G, f)$ can comprise errors linked to line effects.

The capacitance errors corrected by the common equation of the model $C_{cal}(G, f)$ can comprise errors linked to imperfections in the sensor.

The correction model of common equation $C_{cal}(G, f)$ can moreover be arranged in order to eliminate uncertainty regarding the gradient of the systematic polarization development as a function of the excitation frequency.

The correction model of common equation $C_{cal}(G,f)$ can moreover be arranged in order to eliminate the product of the combined effect of the aeration of the medium and overall errors of the electronics within the device.

The coefficients of the correction model $C_{cal}(G,f)$ can be determined starting with a calibration operation in a reference medium containing no biological cells, the conductance of which is modified so as to cover the full scale of the conductance range of the device.

Determination of the capacitance error due to random polarization can be carried out at a predetermined frequency $f_1$ chosen to be as low as possible such that determination of the random polarization capacitance error is only slightly influenced by the capacitance of the medium.

When the method according to the invention is implemented for a measurement carried out on a biological cell suspension, the predetermined frequency $f_1$ used for determination of the capacitance error due to the random polarization can be chosen to be less than or equal to 100 kHz.

The random polarization capacitance $Cm\_cor(G, f_1)$ can be calculated at the frequency $f_1$ by the difference between the raw capacitance measurement originating from the device and the correction model $Ccal(G, f_1)$.

The method according to the invention can moreover comprise determination of the capacitance of the dielectric characteristics of the medium at a second predetermined frequency $f_2$.

When the method according to the invention is implemented for a measurement carried out on a biological cell suspension, the second predetermined frequency $f_2$ can be chosen close to the characteristic frequency fc of said suspension, characteristic of the β dispersion of the cells in suspension.

The capacitance of the dielectric characteristics of the medium $Cm\_cor(G, f_2)$ can be calculated at the frequency $f_2$, by the difference between the raw capacitance measurement originating from the device and the conductance model $Ccal(G, f_2)$.

The method according to the invention can moreover comprise a modelling of the random polarization according to a behaviour model such as $a_{alea} \cdot f^p \cdot G^2$, in which:

G is the conductance of the medium,
$a_{alea}$ is a predefined constant,
p is the polarization gradient.

The determination of the capacitance of the dielectric medium can implement a correction model resulting from a combination:
  of the random polarization capacitance measurement $Cm\_cor(G, f_1)$, estimated at the first predetermined frequency $f_1$,
  of the capacitance measurement of the medium $Cm\_cor(G, f_2)$, estimated at the second predetermined frequency $f_2$,
  and of the behaviour model of the random polarization $a_{alea} \cdot f_p \cdot G^2$.

When the method according to the invention is implemented for the measurement of biological cell suspensions according to a behaviour model of the type $$\text{capacitance } Cx(G,f) = \Delta C_{cell} \times 1/(1+(f/f_c)^2)$$

where $f_c$ is the characteristic frequency of the medium, this frequency characteristic $f_c$ can be either predetermined from a calculation chart, or determined in line by a method for the determination of characteristic parameters of the β dispersion.

The dielectric measured at the first predetermined frequency $f_1$ is preferably substantially identical to the dielectric measured at the second predetermined frequency $f_2$.

In a particular implementation of the method according to the invention for the measurement of a medium containing biological cells, this method also comprises determination of a capacitance error $Cm\_cor(G, f_3)$ due to the thermal drift of the offset of the electronics and to variations in the capacitance of the dielectric suspension medium, at a third predetermined frequency $f_3$.

The capacitance error $Cm\_cor(G, f_3)$ can be calculated at the third predetermined frequency $f_3$ by the difference between the raw capacitance measurement originating from the device and the correction model $Ccal(G, f_3)$.

The method according to the invention can moreover comprise a correction of raw or corrected capacitance measurements, contaminated with errors due to the thermal drift of the offset of the electronics and to variations in capacitance of the suspension medium, by subtracting from these measurements the capacitance error $Cm\_cor(G,f_3)$.

It can also comprise conversion of the capacitance and conductance values of the medium to permittivity and conductivity values, by multiplication of said capacitance and conductance values by a probe factor $k_a$ which is determined from division of the conductivity value of a liquid solution of known conductivity by a conductance measurement value of said solution.

The method according to the invention can moreover comprise determination of a probe factor $k_a$ linked to the aeration of the medium, at a fourth predetermined frequency $f_4$.

The fourth predetermined frequency can be chosen such that the dielectric is the most stable whatever the changes in environmental parameters.

The probe factor $k_a$ advantageously represents an apparent geometric modification of the sensor when bubbles are present in the dielectric medium.

The method according to the invention can also comprise determination of the capacitance $Cm\_cor(G, f_4)$ linked to the factor $k_a$ at the frequency $f_4$ by comparison of the raw capacitance measurement with the conductance model $Ccal(G, f_4)$. The probe factor $k_a$ is for example calculated by relating the capacitance variation $Cm\_cor(G, f4)$ to a capacitance value of a non-aerated reference medium.

The probe factor $k_a$ can be used in order to determine the corrected permittivity of the dielectric medium from the effects of aeration on the capacitance measurement, and in order to determine the conductivity of the medium by correcting the effects of aeration on the conductance measurement.

The method according to the invention can moreover comprise determination of the concentration of biomass of the medium, by multiplying the permittivity measured at the second predetermined frequency $f_2$ by a predetermined coefficient γ which can be determined either using a calculation chart of physical parameters characteristic of biological cells, or using a previous calibration in a suspension medium the concentration of which is known.

It can also be advantageously envisaged that the method according to the invention also comprises determination of parameters characteristic of a dielectric dispersion on media containing biological cells, by using at least three predetermined frequencies $f_5$, $f_6$, $f_7$, as well as determination of capacitances linked to the dispersion Cm_cor(G, $f_5$), Cm_cor(G, $f_6$), Cm_cor(G, $f_7$), at the at least three predetermined frequencies $f_5$, $f_6$, $f_7$, by comparing raw capacitance measurements originating from the device to the conductance models at the corresponding frequencies Ccal(G, $f_5$), Ccal(G, $f_6$), and Ccal(G, $f_7$).

Determination of the parameters characteristic of the dielectric dispersion can comprise:
measurement of a number n of corrected capacitance values Cm_cor(G, $f_{5\ to\ m}$) with m=5+n−1, at n frequencies distributed over the frequency range corresponding to that of the dielectric dispersion studied, n being greater than or equal to 3,
adjustment of a multilinear function dependent on frequency and comprising n variable coefficients in order best to approach the n values of measured corrected capacitance,
calculation of the parameters characteristic of the dielectric dispersion from the coefficients of the multilinear function.

The multilinear function dependent on the frequency can be constituted by a polynomial of degree n−1. The method according to the invention can moreover comprise a calculation of an evaluation of the concentration of biomass of the medium, from the values of the coefficients of the polynomial of degree n−1, as well as a calculation of the evaluation of the size of the microorganisms in the medium, from the coefficients of the polynomial of degree n−1.

According to another aspect of the invention, a device is proposed for determining characteristics of a dielectric medium, implementing the method according to the invention, comprising means for correcting a capacitance signal originating from a device generating a capacitance and conductance signal, this device being linked to a sensor having conductive electrodes in direct contact with the dielectric medium to be measured, this capacitance signal being contaminated with capacitance errors due to random polarization and capacitance errors due to systematic polarization.

According to the invention, the means of correction of the capacitance signal are arranged in order to separately correct on the one hand the capacitance errors due to random polarization and on the other hand the errors due to systematic polarization, and comprise:
means for modelling systematic polarization and capacitance errors including errors due to systematic polarization, in the form of a common equation $C_{cal}(G, f)$, a function of the conductance of the medium and excitation frequency of the conductive electrodes, this equation being arranged in order to eliminate the product of the combined effect of polarization and of the overall errors of the electronics within the device, and,
means for determining a corrected capacitance value Cm_cor(G, f), by comparing each raw capacitance measurement Cx(G, f) originating from the device and carried out at a predetermined frequency, with the value of said common equation of the model $C_{cal}(G, f)$ at said predetermined frequency.

Moreover, this device can also comprise means for determining the capacitance error due to random polarization at a first predetermined frequency $f_1$ chosen to be as low as possible such that determination of the random polarization capacitance error is only slightly influenced by the capacitance of the medium, as well as the means for determining the capacitance of the dielectric characteristics of the medium at a second predetermined frequency $f_2$ chosen to be close to the characteristic frequency fc of the medium, characteristic of the b dispersion of the cells in suspension.

The means for determining the capacitance of the dielectric characteristics of the medium can implement a correction model resulting from a combination:
of a capacitance measurement of random polarization Cm_cor(G, $f_1$), estimated at the first predetermined frequency $f_1$,
of a capacitance measurement of the medium Cm_cor(G, $f_2$), estimated at the second predetermined frequency $f_2$,
and of a behaviour model of random polarization $a_{alea} \cdot f^p \cdot G^2$.

The device according to the invention, used for measuring a medium containing biological cells, can also comprise means for determining a capacitance error Cm_cor(G, $f_3$) due to the thermal drift of the offset of the electronics and to variations in the capacitance of the dielectric suspension medium, at a third predetermined frequency $f_3$, as well as means for determining a capacitance Cm_cor(G, $f_4$) linked to a probe factor $k_a$ linked to the aeration of the medium, at a fourth predetermined frequency $f_4$.

It can also comprise means for determining parameters characteristic of a dielectric dispersion on media containing biological cells, by using at least three predetermined frequencies $f_5$, $f_6$, $f_7$.

In a particular version of the invention, the device also comprises means for determining parameters characteristic of the dielectric dispersion, comprising:
means for measuring a number n of corrected capacitance values Cm_cor(G, $f_{5\ to\ m}$) at n frequencies distributed over the frequency range corresponding to that of the dielectric dispersion studied, n being greater than or equal to 3,
means for adjusting a multilinear function dependent on frequency and comprising n variable coefficients for best approaching the n measured corrected capacitance values, and
means for calculating parameters characteristic of the dielectric dispersion from the coefficients of the multilinear function.

According to yet another aspect of the invention, a device is proposed for measuring a biomass of a biological medium, implementing a method for dielectric determination according to the invention, and/or including a device for dielectric determination according to the invention.

Within the scope of the present invention an impedance measurement device is also proposed, arranged in order to provide a measurement of the real part of an impedance and of the capacitance corresponding to this impedance, including a device for measuring characteristics of a dielectric medium according to the invention.

BRIEF DESCRIPTION OF THE DRAWING FIGURES

Other advantages and characteristics of the invention will become apparent on examination of the detailed description of a method of implementation which is in no way limitative, and the attached drawings in which.

DETAILED DESCRIPTION OF THE INVENTION

A detailed description will first be given of the physical principles on which the determination method is based, by presenting an analysis of the different sources of capacitance error encountered in a biomass measurement device of the type described in the document FR2812725.

The method according to the invention proposes an overall correction of the parasitic effects of the electronics and the electrode polarization effects.

Figure 4:
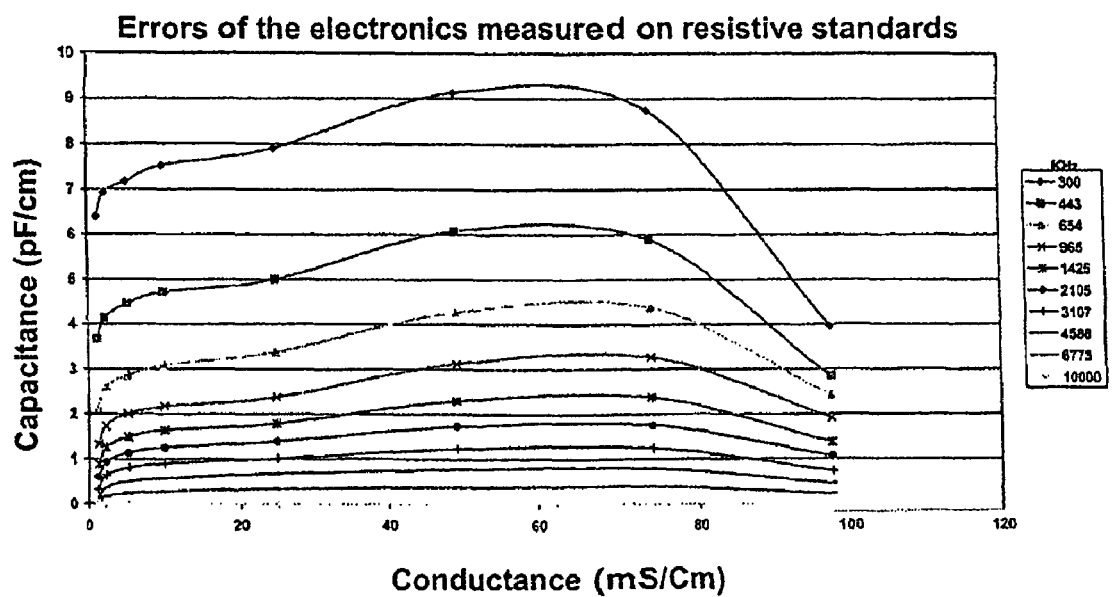
FIGS. 4, 5 and 6 represent, at different frequencies, the capacitive errors due to imperfections in the electronics, sensor and line effects respectively.
Figure 5:
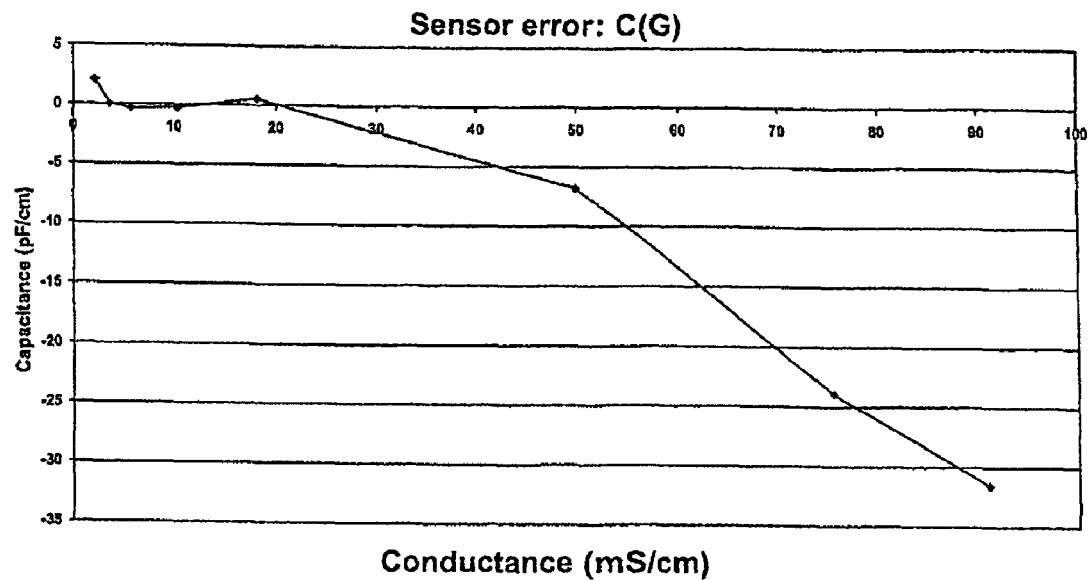
Figure 6:
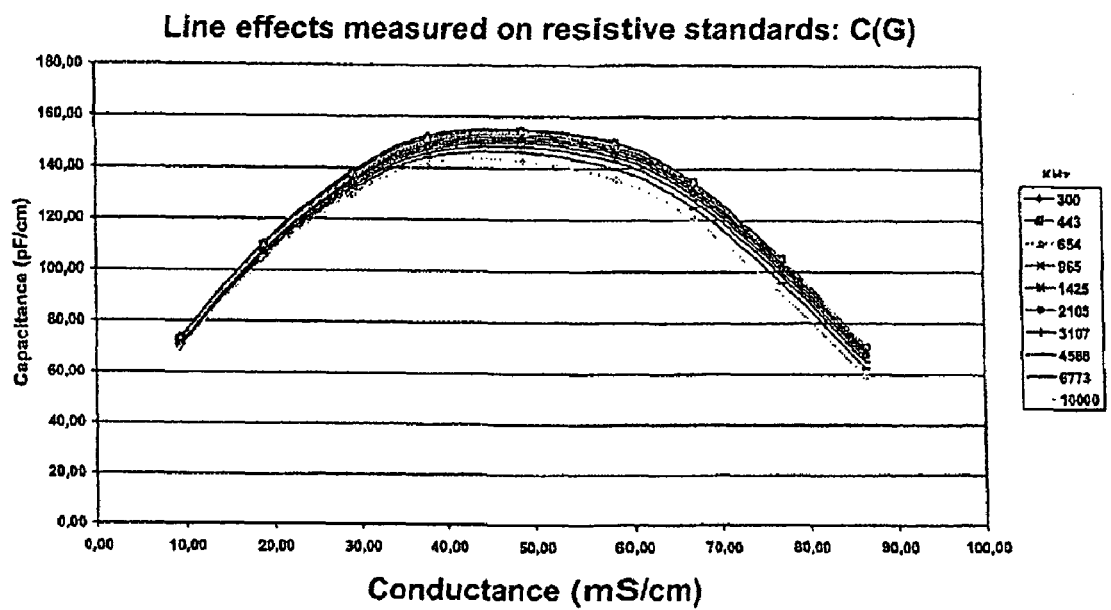
Figure 7:
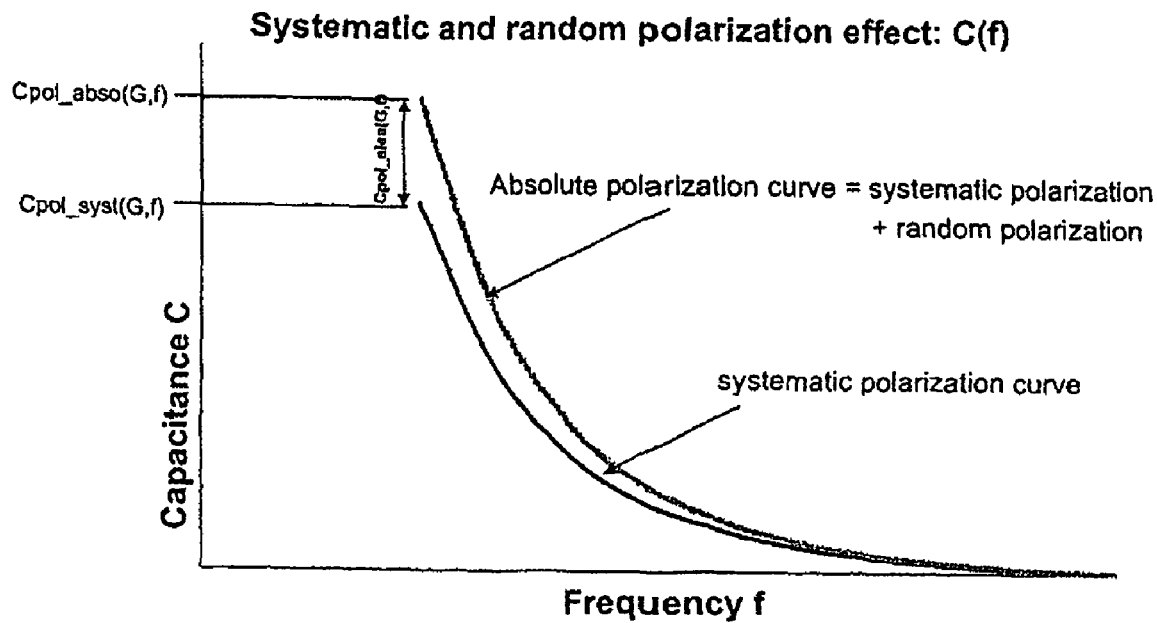
FIG. 7 represents on the same graph an absolute polarization curve (systematic polarization+random polarization) and a systematic polarization curve.

The capacitive errors typically encountered in a biomass measurement device are the following:

errors in the measurement electronics, as illustrated in FIG. 4. These errors, the amplitude of which can reach approximately 10 pF/cm, vary as a function of the conductance G and of the frequency. They are generated by a very large number of components, which makes them difficult to correct in theory. From the main factors involved in these errors, there can be mentioned the phase errors of the components, the inductive effects of the tracks, and the non-linear errors of the components;

sensor errors, as illustrated in FIG. 7. Apart from the polarization effect, the sensor errors are mainly inductive in nature, can reach 30 pF/cm, and vary as a function of the frequency;

line effect errors, as illustrated in FIG. 6. Apart from the polarization effect, these are the greatest errors encountered in a biomass measurement device of the type of that described in the document FR2812725. They can reach 150 pF/cm.

They vary mainly as a function of frequency and conductance G.

The result of the measurement of permittivity in a dielectric medium is the consequence of all of the electronic phenomena presented, to which are added the electrode surface polarization phenomena. All these phenomena each have their own behaviour as a function of conductance and frequency and sometimes exhibit non-linear behaviour as in the case of the electronics.

It is therefore necessary to develop a method for extracting the information "permittivity of the medium" from the overall capacitance signal. For the biomass measurement, the difficulty of extraction of the measurement "permittivity of the biomass" is still greater. Biological cells have their own frequency response, which will be added to the different spectral responses of the equipment and the polarization of the sensor.

In-line calculation methods already exist, which mostly correct only polarization errors. In fact, the biomass measurement systems are generally provided with electronics arranged as close as possible to the electrodes, in accordance with good engineering practice. The line effects are then much lower than those observed in a system where the electronics are distant in relation to the electrodes, and therefore do not require a method combining correction of polarization and line effect.

A method for biomass determination is already known, developed by Bordi et al. (op. cit.), which uses a general formula which is the result of the combination of models of physical, chemical, biological and electronic operation. However, this results in very heavy use as it is necessary to determine all the coefficients originating from these models. Moreover, a regression method must be put in place in order to compare the overall formula with the capacitance measurement spectrum. The spectrum must comprise a high number of frequencies in order to identify all the parameters.

The method according to the invention makes it possible to determine the permittivity of a dielectric medium from a capacitance signal and a conductance signal, containing the capacitive errors of the electronics, line effects, sensor and electrode polarization.

In simplified manner, the method according to the invention consists of correcting the capacitance measurements using the conductance measurements carried out simultaneously by the device. In fact, we have shown, starting with theoretical considerations and experimental measurements, that all the errors, whether they are polarization errors or errors linked to the imperfections in the device, could be expressed as a function of the conductance of the medium. Each capacitance measurement is therefore corrected by subtracting from it a correction value calculated from the conductance, using an equation established at the end of a previous calibration operation. A second level of correction then makes it possible to eliminate the residual errors in order to produce a calculated capacitance value which no longer depends only on the dielectric properties of the medium studied.

These measurements signals and the errors of the electronics are written as follows:

$$Cm(G,f)=Cx(G,f)+\text{Celec\_ampli}(G,f)+\text{Celect\_lin}(G,f)+\text{Celec\_sens}(G,f)+\text{Cpol\_syst}(G,f)+\text{Cpol\_alea}(G,f) \quad (1)$$

with:
Cm(G, f): raw capacitance signal
Cx(G, f): capacitance of the dielectric medium (biomass) itself
Celec_ampli(G, f): capacitance of the measurement electronics
Celect_lin(G, f): capacitance of the line effect
Celec_sens(G, f): capacitance of the sensor
Cpol_syst(G, f): systematic polarization capacitance
Cpol_alea(G, f): random polarization capacitance.

With reference to the abovementioned figures, the main stages of implementation of the determination method according to the invention will now be described.

First Correction Level

Elimination of Errors Linked to the Electronics and to Systematic Polarization

Stage 1: Global Model of the Electronics

The global model of the electronics was produced following a study of the electronic errors of a biomass measurement device, showing that the curves of the capacitive errors (electronics, line effects and errors linked to the sensor) have shapes dependent on the conductance which remain unchanged whatever the dielectric medium measured. By contrast, these curves vary with the frequency used.

It follows from this that, in order to be free of the overall effects of the electronics and before any other processing, the raw capacitance signal should be corrected, by subtracting from it a value Celec_mod(G, f), calculated from a global behaviour model, dependent on the conductance (2), for each of the measurement frequencies used.

$$Celec\_mod(G,f) = Celec\_ampli(G,f) + Celect\_lin(G,f) + Celec\_sens(G,f) \quad (2)$$

The capacitive errors of the sensor and the line effects are mainly due to inductive-type (inductive) errors. It has been theoretically demonstrated that this type of error generates on the capacitance measurement an error proportional to $-L \cdot G^2$ (L: value of self induction, and G: value of the conductance which charges the self induction). This model makes it possible to correct a very high percentage (typically 90%) of the errors of the electronics of the biomass measurement device. In order to correct the residual error and the errors of non-linearity of the electronics, in practice a polynomial equation of order 3 or 4 is used, as a function of the conductance (3), calculated by the least squares method, according to a procedure which will be described shortly hereafter. Use of a polynomial of a different order or of other types of models, depending on conductance, could be envisaged. The expression used for the first correction stage is therefore the following:

$$Celec\_mod(G,f) = e_{f,0} + e_{f,1} \cdot G + e_{f,2} \cdot G^2 + e_{f,3} \cdot G^3 \quad (3)$$

with:

$e_{f,1}$: coefficients predetermined for a given frequency
G: conductance of the medium

Stage 2: Global Model Correcting the Effect of Systematic Polarization and the Overall Errors of the Electronics This second correction stage uses a model correcting systematic polarization separately from random polarization. The absolute polarization Cpol_abso(G, f) is the sum of the two polarizations, systematic and random respectively, with reference to FIG. 7.

$$Cpol\_abso(G,f) = Cpol\_syst(G,f) + Cpol\_alea(G,f) \quad (4)$$

Systematic polarization Cpol_syst(G, f) is the polarization which is observed in a reference bath which contains no biological cells and in which the conductance is varied with a view to calibration of the device. This operation is carried out only once.

Random polarization Cpol_alea(G, f) is the polarization modification which is observed at a given instant, with respect to systematic polarization. This modification is unforeseeable with regard to time.

Figure 1:
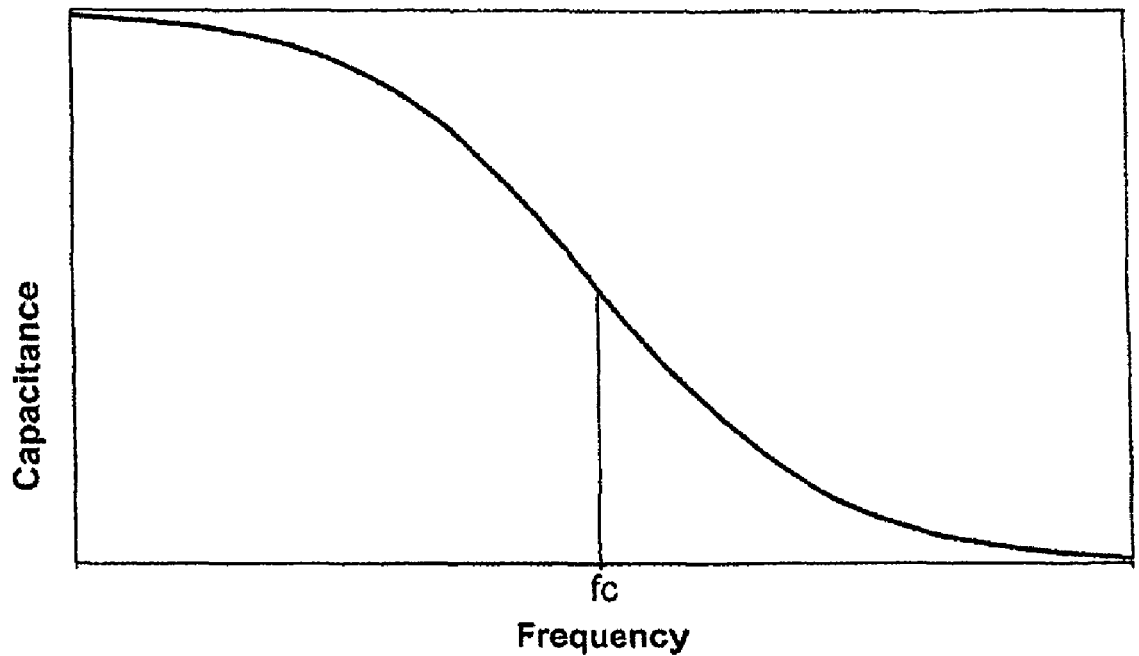
FIG. 1 represents a model of the behaviour of biological cells with a β dispersion.
Figure 2:
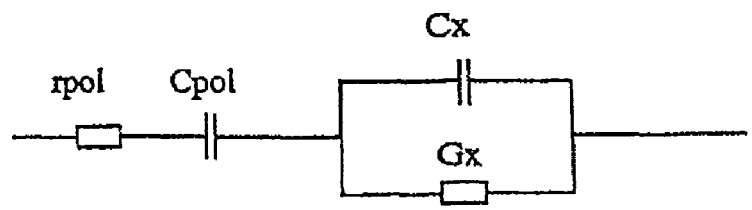
FIG. 2 illustrates a conventional electric model of the effects of polarization of electrodes.
Figure 3:
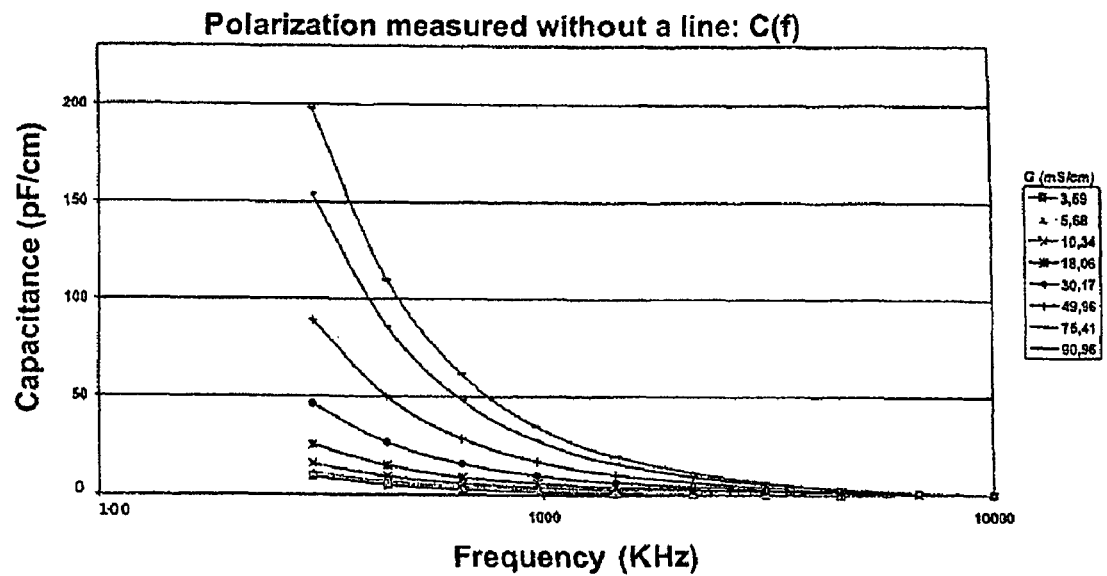
FIG. 3 illustrates a development of a polarization capacitance measured without a line, as a function of the frequency.

The electrochemical model of systematic polarization is the known Nernst double layer model. Its equivalent electronic diagram is shown in FIG. 2, with:

rpol: polarization resistance
Cpol: double layer polarization capacitance
Cx: capacitance of the medium
Gx: conductance of the medium By calculating the effect of the polarization capacitance Cpol on the measurement Cx from this electrochemical model we find:

$$Cpol\_syst(G,f) = a_{sys} \cdot f^p \cdot G^2 \quad (5)$$

with:

G: conductance of the medium
$a_{sys}$: predefined constant (in general equal to 1/systematic polarization capacitance)
p: constant corresponding to the polarization gradient (in general equal to $-2$)

As for electronics errors, it is observed that for a fixed frequency, the effect of polarization varies only as a function of the conductance. Two types of errors have therefore been combined, which allows the use of a common model of capacitance error as a function of G, which combines the overall error of the electronics and the systematic polarization error.

$$Ccal(G,f) = Celec\_mod(G,f) + Cpol\_syst(G,f) \quad (6)$$

$$Ccal(G,f) = e_{f,0} + e_{f,1} \cdot G + (a_{sys} \cdot f^p + e_{f,2}) \cdot G^2 + e_{f,3} \cdot G^3 \quad (7)$$

a polynomial of the following form is then obtained:

$$Ccal(G,f) = a_{f,0} + a_{f,1} \cdot G + a_{f,2} \cdot G^2 + a_{f,3} \cdot G^3 \quad (8)$$

with:

$a_{f,i}$: predetermined coefficients for a given frequency
G: conductance of the medium Use of a polynomial of a different order or another type of conductance model could be envisaged. A non-linear model could be used if for example the electronics or the polarization had a non-linear behaviour as a function of the conductance.

This method has the advantage of also eliminating the second order effects such as the product of the combined effect of polarization and the overall errors of the electronics, such as uncertainty regarding the value of the systematic polarization gradient (fixed at $-2$), and such as the product of the combined effect of the aeration of the medium with the overall errors of the electronics.

The coefficients of the model (8) must be determined experimentally for each measurement frequency used by the biomass measurement device. This is achieved by a calibration operation in a reference medium containing no biological cells and in which the conductance of the medium is varied throughout the range of the device. The conductance and capacitance values obtained make it possible to calculate the coefficients of the model (8).

If the permittivity of this reference medium is known, it can then be subtracted from the capacitance measurements before calculation of the coefficients. This makes it possible to obtain a correction model, as a function of the conductance and free from the capacitance of the reference medium. In the opposite case, the correction operations will lead to capacitance values relating to that of the reference medium.

A description will now be given of the principle of processing the raw capacitance signals implemented in the method according to the invention. For the remainder of the implementation of the method according to the invention, the following principle will be used to process the raw capacitance signals: The value calculated starting with the model Ccal(G, f) (8) is subtracted from the measured raw capacitance signal Cm_(G, f). A corrected capacitance measurement Cm_cor(G, f) is obtained $$Cm\_cor(G,f) = Cm(G,f) - Ccal(G,f) \quad (9)$$

It will be recalled that this operation makes it possible to correct 90% of the errors due to both the systematic polarization and the errors linked to the material imperfections. After combination of the equations (1), (2), (4) and (6) we find:

$$Cm\_cor(G,f) = Cx(G,f) + Cpol\_alea(G,f) \quad (10)$$

The corrected capacitance measurement is therefore equal to the sum of the capacitance of the studied dielectric medium and the random polarization error.

Second Correction Level: Correction of the Random Polarization Error

Stage 3: Determination of Random Polarization at Frequency $f_1$

The random polarization capacitance is determined at a single measurement frequency. It is obtained by subtracting from the capacitance measurement carried out at low frequency $f_1$ a value calculated from the calibration model Ccal (G, f)(8) according to the principle of processing the raw capacitance measurements (cf. FIG. 7).

In the case of a medium containing biological cells, this subtraction leads only to an estimation of random polarization, as the quantity of biomass contained in the medium Cx(G, f1) also influences this result.

The following is obtained:

$$\text{Cpol\_alea}(G,f_1) = \text{Cm\_cor}(G,f_1) - Cx(G,f_1) \quad (11)$$

If it is considered that random polarization results from the adsorption of compounds which modify in one direction or the other the thickness of the Nernst ionic double layer, which is responsible for systematic polarization, it is easily demonstrated that the variation in random polarization as a function of the measurement frequency and of the conductance of the medium is proportional to $G^2/f^2$. (5). This random polarization behaviour hypothesis was confirmed from experiments carried out with a biomass measurement device of the type described in the document FR2812725.

The following relationship is then obtained experimentally:

$$\text{Cpol\_alea}(G,f) = a_{alea} \cdot f^p \cdot G^2 \quad (12)$$

With:
G: conductance of the medium
$a_{alea}$: predefined constant (in general equal to 1/random polarization capacitance)
p: constant corresponds to the polarization gradient (in practice very close to the theoretical value equal to −2)

The measurement frequency of the random polarization must be chosen to be very low in order that, by means of the term in $1/f^2$ (12), the value measured is the highest possible given the capacitance of the biomass in the medium. In practice, a measurement frequency of 100 Khz allows excellent determination of the random polarization capacitance.

This can then be expressed:

$$\text{Cpol\_alea}(G,fi) \text{Cm\_cor}(G,f_1) \quad (13)$$

Stage 4: Estimation of the Capacitance of the Medium at Frequency $f_2$

A capacitance measurement, characteristic of the dielectric medium studied, is carried out at a second frequency $f_2$. It is obtained by subtracting from the capacitance measurement a value calculated from the calibration model Ccal(G, f) (8) according to the principle of processing the raw capacitance measurements. In the case of measurements carried out on biological cells, this frequency is preferably chosen close to the characteristic frequency fc of the cell, according to the model proposed by Pauly and Schwan.

This subtraction gives the value of the capacitance characteristic of the dielectric medium studied, to which is also added the value of random polarization capacitance at frequency $f_2$:

$$\text{Cm\_cor}(G,f_2) = Cx(G,f_2) + \text{Cpol\_alea}(G,f_2) \quad (14)$$

Stage 5: Correction of Random Polarization on the Measurement of Capacitance at Frequency $f_2$ The equations of the random polarization capacitance (11) and the estimation of the characteristic capacitance of the dielectric medium studied (14) are then combined.

The values of the random polarization capacitance (12) at the two frequencies $f_1$ and $f_2$ are:

$$\text{Cpol\_alea}(G,f_1) = a_{alea} \cdot f_1^p \cdot G^2$$

$$\text{Cpol\_alea}(G,f_2) = a_{alea} \cdot f_2^p \cdot G^2$$

By dividing these two equations we find:

$$\text{Cpol\_alea}(G,f_2) = \text{Cpol\_alea}(G,f_1) \cdot (f_2/f_1)^p \quad (15)$$

The combination of equations (11), (14) and (15) leads to the following expression:

$$Cx(G,f_2) = \text{Cm\_cor}(G,f_2) - (f_2/f_1)^p \cdot [\text{Cm\_cor}(G,f_1)] + [Cx(G,f_1)] \cdot (f_2/f_1)^p \quad (16)$$

The combination of equations (9) and (15) leads to equation (17) expressed hereafter which provides the calculation formula for the capacitance of the dielectric medium studied, corrected for all the effects of polarization and electronics. This result is referred to hereafter as the "FG correction method".

General Formula of the FG Correction Method $$Cx(G,f_2) = \text{Cm\_}(G,f_2) - \text{Ccal}(G,f_2) - (f_2/f_1)^p \cdot [\text{Cm\_}(G,f_1) - \text{Ccal}(G,f_1)] + [Cx(G,f_1) \cdot (f_2/f_1)^p] \quad (17)$$

with:
Cx(G, $f_2$): capacitance of the dielectric medium at frequency $f_2$
Cm_(G, $f_2$): raw capacitance measured at frequency $f_2$
Ccal(G, $f_2$): capacitance as a function of G, measured in a reference medium at frequency $f_2$
Cm_(G, $f_1$): raw capacitance measured at frequency $f_1$
Ccal(G, $f_1$): capacitance as a function of G measured in a reference medium at frequency $f_1$
Cx(G, $f_1$): capacitance of the dielectric medium at frequency $f_1$
$f_1$: frequency at which random polarization capacitance is estimated
$f_2$: measurement frequency of the characteristic capacitance of the dielectric medium
p: constant corresponding to the polarization gradient (in general equal to −2)

In this formula (17), the term [Cx(G, fi)], introduces an error as it is not known. This term can be made negligible by a choice of the lowest possible polarization measurement frequency $f_1$, as explained previously. A frequency of 100 KHz produces very good results.

For example a measurement frequency $f_2$=1000 KHz divides by 100 this error term by means of the term in factor $(f_2/f_1)^p$.

The advantages of this FG correction method are therefore:
overall correction of the errors of the electronics and the effects of systematic and random polarization,
correction also of second order effects, such as the product of the combined effect of polarization with the overall errors of the electronics, uncertainty regarding the value of the systematic polarization gradient (fixed at −2), and the product of the combined effect of the aeration of the medium with the overall errors of the electronics,
use of a calibration method which makes it possible to determine in one go the parameters of a global correction model, integrating the effects of the electronics and systematic polarization, this calibration method being carried out, in an automatable manner, in a reference medium without biological cells, correction of absolute polarization at frequency $f_2$ in a more precise manner than the existing digital methods; the correction is less influenced by an error on the polarization gradient p or drift of the frequencies $f_1$ or $f_2$, as the electrochemical model of type $a \cdot f^p \cdot G^2$ is applied only for random polarization, which is only a relatively small proportion (approximately 10% maximum) of the absolute polarization;

implementation of a correction formula (17) which uses only simple operators and can therefore be easily implanted in an embedded system, and use of only a single frequency in order to determine the random polarization capacitance.

Improvements in the quality of this correction method can be envisaged. We shall show that the formula of the FG correction method (17) can be modified depending on the type of dielectric which is to be measured, by presenting two non-limitative examples of implementation of the FG correction method.

EXAMPLE 1

If the capacitance of the dielectric medium measured does not vary as a function of the frequency, then:—

$$Cx(G, f_2) = Cx(G, f_1)$$

Formula (17) is then simplified, to produce the correction method formula FG_B:

$$C_{X\_FG\_B}(G, f_2) = [Cm\_G, f_2) - Ccal(G, f_2) - (f_2/f_1)^p \cdot [Cm\_(G, f_1) - Ccal(G, f_1)]]/[1 - (f_2/f_1)^p] \quad (18)$$

All the terms in this formula FG_B are explicitly known.

EXAMPLE 2

If the dielectric medium to be measured is a biological cell suspension, the formula of the FG correction method (17) can be expressed in the form:

$$Cx(G, f_2) \cdot [1 - (f_2/f_1)^p \cdot Cx(G, f_1)/Cx(G, f_2)] = Cm\_(G, f_2) - Ccal(G, f_2) - (f_2/f_1)^p \cdot [Cm\_(G, f_1) - Ccal(G, f_1)] \quad (19)$$

By using the Pauly and Schwann model and by considering that the capacitance of the medium is negligible given the measured capacitance, we have:

$$Cx(G, f_1) = \Delta C_{cell}/(1 + (f_1/f_c)^2)$$

$$Cx(G, f_2) = \Delta C_{cell}/(1 + (f_2/f_c)^2)$$

with fc: characteristic frequency of the biological cell.

By dividing these two equations, we find that:

$$Cx(G, f_1)/Cx(G, f_2) = (1 + (f_2/f_c)^2)/(1 + (f_1/f_c)^2) \quad (20)$$

The combination of equations (19) and (20) and a gradient equal to −2 leads to an FG_C correction method formula:

$$C_{X\_FG\_C}(G, f_2) = (1 + f_1^2/f_c^2) \cdot 1/(1 - f_1^2/f_2^2)[Cm\_(G, f_2) - Ccal(G, f_2) - (f_2/f_1)^p \cdot [Cm\_(G, f_1) - Ccal(G, f_1)]] \quad (21)$$

This formula, adapted to biological media, is significantly more effective than the basic FG method (17). The main correction term for the biological medium is in practice $1/(1 - f_1^2/f_2^2)$. It corresponds to the hypothesis of equality of value for the two capacitances measured at frequency $f_1$ and $f_2$, as in the preceding example.

The term $(1 + f_1^2/f_2^2)$ provides a less significant correction. It can be replaced by 1 in the majority of cases. Another solution is to give it an indicative value. For cases where it would be used in order to refine the measurement, it is necessary to know the characteristic frequency fc of the medium used, either by calculating it from the theoretical equation $$fc = 1/(4 \cdot p \cdot r \cdot Cm \cdot (1/sc - 1/sm))$$

in which s m is the conductivity of the medium, determined from the conductance G measured by the device, the other parameters Cm and s c are estimated from the scientific literature (1 μF/cm and 3 mS/cm respectively), and r is the radius of the biological cells studied, assumed to be spherical, or by an in-line method allowing the evaluation of fc from measurements at different frequencies, corrected by the FG method. The capacitance measurements and the evaluation of fc can then be refined in a few iterations.

Third Correction Level: Correction of Offset Drifts and Variations in Capacitances of the Medium (Excluding Biomass)

Stage 6: Suppression of the Offset Drift of the Electronics

Once the capacitance signal is corrected by the FG method, a slight thermal drift of this signal remains, which is due to the offset drift of the electronics. This error is corrected using the capacitance measurement carried out at a third frequency. The highest frequency of the device (for example, 10 MHz) is used for this purpose as, in this case, it offers the advantage of also suppressing any variation in capacitance of the dielectric medium which would be linked to a development of the biological cell suspension medium.

According to the principle of processing the raw capacitance measurements, the corrected term is obtained:

$$Cm\_cor(G, f_3) = Cm(G, f_3) - Ccal(G, f_3)$$

This correction term must be subtracted from the FG correction method which is to be used.

For example, starting from the FG_C correction method (21) we arrive at the FG_C0 correction method:

$$\Delta CX(G, f_2)(1 + f_1^2/f_c^2) \cdot 1/(1 - f_1^2/f_2^2) - [Cm\_(G, f_2) - Ccal(G, f_2) - (f_2/f_1)^p[Cm\_(G, f_1) - Ccal(G, f_1)]] - (Cm\_(G, f_3) - Ccal(G, f_3)) \quad (22)$$

with:
$\Delta Cx(G, f_2)$: capacitive increment of the dielectric medium at frequency $f_2$
$Cm\_(G, f_2)$: raw capacitance measured at frequency f2
$Ccal(G, f_2)$: capacitance as a function of G, measured in a reference medium at frequency $f_2$
$Cm\_(G, f_1)$: raw capacitance measured at frequency $f_1$
$Ccal(G, f_1)$: capacitance as a function of G measured in a reference medium at frequency $f_1$
$Cx(G, f_1)$: capacitance of the dielectric medium at frequency $f_1$
$f_1$: frequency at which the random polarization capacitance is estimated
$f_2$: measurement frequency of the characteristic capacitance of the dielectric medium
p: constant corresponding to the polarization gradient (in general equal to −2)
$f_3$: frequency at which the thermal drift of the offset of the electronics and the capacitance of the dielectric medium (excluding cells) is measured
$f_c$: characteristic frequency (Pauly and Schwann) of the biological medium studied This FG_C0 correction method formula was implanted in a biomass measurement device of the type of that described in the document FR2812725. This formula makes it possible to correct:
- all of the capacitance errors, functions of frequency and conductance, of the electronics, line effects, and sensor, systematic and random polarization errors,
- the thermal drift of the offset of the electronics,
- the variation in the capacitance of the dielectric medium (excluding biological cells).

Stage 7: Determination of the Permittivity and Conductance of the Dielectric Medium The measured capacitance and conductance values are converted to absolute permittivity and conductivity respectively by multiplying the capacitance values and the conductance values by a probe factor k.

$$e = C \cdot k \text{ and } s = G \cdot k \tag{23}$$

This factor k is constant for a given sensor geometry. It is equal to L/S in the case of a plane capacitor having an electrode surface area S and an inter-electrode distance L.

In the case of the biomass measurement device of the type described in the document FR2812725, the factor k is determined experimentally using a solution of salt water of known conductivity. Determination of the factor k is achieved by dividing the conductivity value of the solution by the conductance measured by the device.

This probe factor k can be applied to the conductance and capacitance measurements before or after correction of these measurements by the FG correction method.

Applied to the value of $\Delta CX(G, f_2)$ obtained previously (Equation 22), it makes it possible to obtain the permittivity increment $\Delta \in$ with $$\Delta \in = \Delta C_x(G, f_2) \cdot k \tag{24}$$

Stage 8: Determination of the Biomass Concentration

The amplitude of the β dispersion, for cells assumed to be spherical, to the extent that the volume fraction P is not too great (as is the case in the majority of fermentations) is provided by the standard relationship:

$$\Delta \varepsilon = \frac{9}{4} r C_m P \tag{25}$$

in which $\Delta \in$ here represents the permittivity increment calculated by finding the difference between permittivity at low frequency and permittivity at high frequency, on either side of the β dispersion. This relationship is also valid when the "low" permittivity is taken at any frequency beyond the high frequency, in the β dispersion range, and in particular at frequency $f_2$, as defined previously.

For a microbial biomass, it can be considered that there is proportionality between the concentration of biomass X and the volume fraction P, by adopting the hypothesis that the membrane capacitance Cm and the radius r are constants. Thus the following relationship is obtained $$X = \gamma \cdot \Delta \in \tag{26}$$

with:
γ: biological cell coefficient; this coefficient can be deduced from calibration in a biomass suspension the concentration of which is known;

$\Delta \in$: variation in permittivity calculated according to the equation (24)

Stage 9: Correction of the Effects of Aeration on the Permittivity and Conductance Measurements In an aerated medium, the probe factor k (k=L/S in the case of a plane capacitor with S the electrode surface area and L the inter-electrode distance) increases as the apparent surface area of the electrodes is reduced by the presence of the bubbles. The length of the course of the inter-electrode field lines is increased, but less significantly.

For a dielectric medium of permittivity e and conductivity s, the capacitance and conductance measured are expressed, without aeration and with aeration respectively, as follows:

without aeration:

$$C_0(G_0, f) = e/k \text{ and } G_0 = s/k \tag{27}$$

with aeration:

$$C_a(G_a, f) = e/k_a \text{ and } G_a = s/k_a \tag{28}$$

Combination of equations (27) and (28) gives:

$$k_a = k \cdot C_0(G_0, f)/C_a(G_a, f) = k \cdot G_0/G_a \tag{29}$$

By choosing a predetermined frequency $f_4$ where the value of the dielectric characteristics of the medium is most stable whatever the changes in environmental parameters, it is possible to determine a variation in capacitance linked only to the change in the aeration level. For a medium containing biological cells in suspension, this frequency is to be chosen clearly above the frequency fc, typically between 10 and 100 MHz.

This variation in capacitance is then obtained by subtracting from the capacitance measurement carried out at frequency $f_4$, the value calculated from the calibration model Ccal(G, $f_4$) (8), according to the principle of processing the raw capacitance measurements Cm_cor(G, $f_4$).

$$\text{Cm\_cor}(G_a, f_4) = C_a(G_a, f_4) - C_0(G_0, f_4) \tag{30}$$

The combination of equations (26) and (27) produces the probe factor in an aerated medium:

$$ka = k/[1 + (\text{Cm\_cor}(G_a, f_4)/C_0(G_0, f_4))] \tag{31}$$

with:
- k: probe factor of a non-aerated reference medium
- $C_0(G, f_4)$: capacitance of the non-aerated reference medium at frequency $f_4$. This predetermined value is obtained either by a calculation chart of permittivity of the dielectric materials and by using the probe factor k, or by measuring the capacitance of the non-aerated reference medium according to the principle of processing of the raw capacitance measurements Cm_cor($G_0$, $f_4$)—In general, the permittivity or the capacitance of the reference medium is that of the water.

The probe factor in an aerated medium $k_a$ is then used in order to determine the permittivity of the dielectric medium, corrected for the effects of aeration on the capacitance measurement (32). The conductivity of the medium is also determined by correcting the effects of aeration on the conductance measurement (33).

The combination of equations (25) and (28) produces the permittivity of the medium at all frequencies of the device:

$$e = \text{Cm\_cor}(G_a, f) \cdot k/[1 + (\text{Cm\_cor}(G_a, f_4)/C_0(G_0, F_4))] \tag{32}$$

The conductivity of the medium at all the frequencies of the device is expressed as follows:

$$s = G8 \cdot k/[1 + (\text{Cm\_cor}(Ga, F_4)/C0(G0, F_4))] \tag{33}$$

with:
- e: permittivity determined at frequency f and corrected for the effects of aeration
- s: conductivity determined at frequency f and corrected for the effects of aeration
- Cm_cor(G, f): capacitance measured according to the principle of processing the capacitance measurements, affected by aeration and measured at frequency f
- Cm_cor(G, $F_4$): capacitance measured according to the principle of processing the capacitance measurements, affected by aeration and measured at the frequency of determination of aeration $F_4$
- $C_0(G_0, f_4)$: Capacitance of the reference medium under non-aeration conditions and at frequency $f_4$
- $G_a$: conductance of the medium affected by aeration and measured at frequency $f_4$
- $G_0$: conductance of the reference medium under non-aeration conditions The capacitance and conductance values corrected for aeration can be determined with the equation (27).

Stage 10: Determination of the Characteristic Parameters of a Dielectric Dispersion The method most often used for biomass evaluation, which consists of measuring the capacitance of the medium at one or two predefined frequencies, does not in reality allow direct evaluation of the biovolume. This is in fact the product P·r·Cm, a complex quantity, which is evaluated by the increment $\Delta\in$, which depends simultaneously on the conductivity of the medium, the size and size distribution of the cells, as well as on their physiological state. In order to evaluate the biovolume with a greater probability, it is necessary to extract enough information from the dispersion curve to identify the greatest possible number of variables. The β dispersion curve can be obtained by applying the capacitance measurement correction method described previously.

An explanation is given here, within the framework of the present invention, of a method making it possible to find the mathematical descriptors of the β dispersion, by using for this purpose a linear adjustment technique, whilst the other methods proposed use non-linear adjustment techniques, which are potentially more precise, but much more difficult to implement, in particular if they have to be implanted in microcontroller-based systems.

A polynomial of order n is used in order to represent the curve Cx=f(frequency).
This can be expressed:

$$Cx = P(f) = a0 + a1 \cdot f + a2 \cdot f2 + a3 \cdot f3 + \ldots an \cdot fn$$

Figure 8:
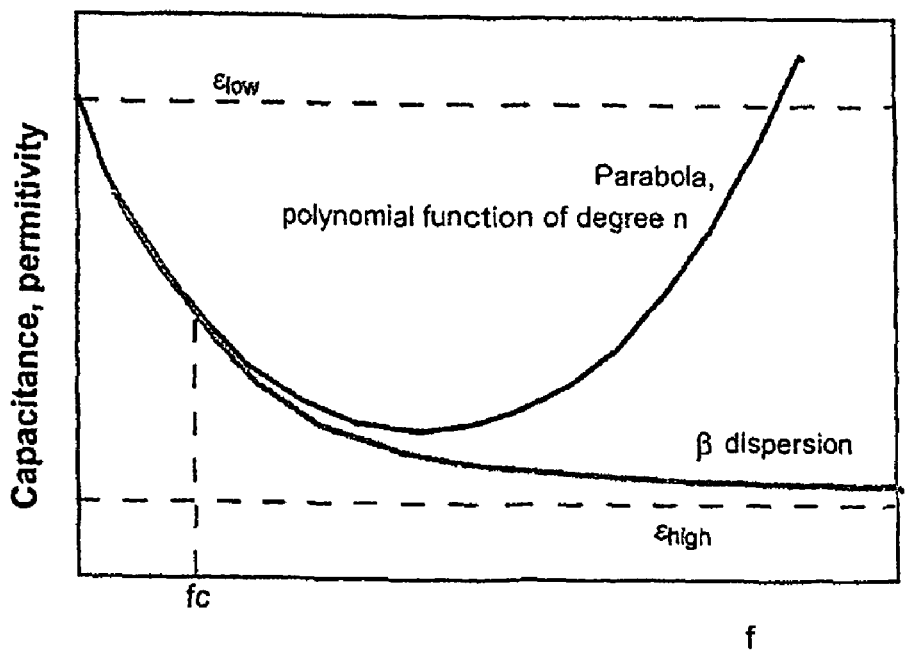
FIG. 8 illustrates the adjustment of a polynomial function of order n over a dispersion curve in its part beyond the characteristic frequency, implemented in the method according to the invention.
Figure 9:
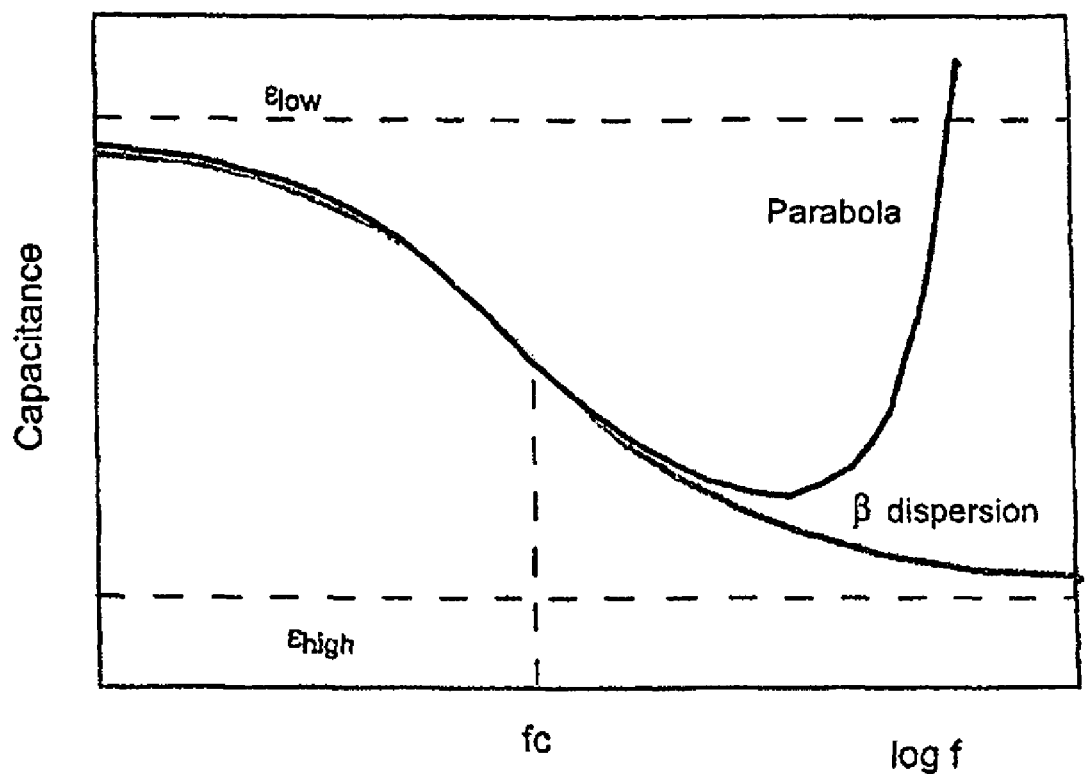
FIG. 9 illustrates adjustment of a polynomial function of order n on a dispersion curve in its part below the characteristic frequency, implemented in the method according to the invention.

A remarkable fact is that from an order n equal to or greater than 2, the polynomial function can be adjusted on the β dispersion curve, on either side of the frequency fc, as illustrated in FIG. 8. In fact, the inflexion of the dispersion curve exists only in semi-logarithmic coordinates. On the side of the high frequencies, the polynomial always has a parabolic branch, which tends towards infinity (+). In principle, this type of function cannot therefore be applied directly to the study of the highest-frequency range, much greater than fc. On the other hand, it is imperative that the measurements include this characteristic frequency, since this is what conditions the determination of the point of inflexion of the β dispersion curve. The polynomial describes the low-frequency range very well and can in particular be calculated in f=0, where $$Cx_{(f=0)} = a0$$

The value of the capacitive increment is thus easily calculated.

A detailed description will now be given of the procedure to be used for calculation of the different coefficients of the polynomial. This will be confined to presentation of the case where n=2. This involves identifying the three coefficients of the function:

$$Cx = a0 + a1 f + a2 f^2$$

At least three measurements are therefore needed, carried out at three frequencies distributed around the characteristic frequency typical of β dispersion. The data published in the scientific literature show that this characteristic frequency is often comprised between 0.5 and 2 MHz. Since the measurement must be extrapolated to f=0, it is desirable to fix a measurement frequency at the lowest technically envisageable value (typically 0.1 to 0.3 MHz), in order to limit the error linked to the extrapolation. On the other hand, it has been observed that the polynomial function poorly represented the high-frequency range. A high frequency equal to 2 or 3 MHz will therefore be used most often. However, in the case of small cells (bacteria for example), for which the characteristic frequency is higher, it is necessary to choose a still higher measurement frequency. The frequency range could be extended by using a polynomial function of a higher order, at the expense of greater complexity and a reduction in the "robustness" of the method.

The method thus reduces to the resolution of a system of three equations (the three measurements) with three unknowns (the three parameters). In matrix form, the problem is written:

$$[C]=[F]\times[Coeffs], \text{ which is resolved to } [Coeffs]=[F]^{-1} \cdot C$$

The coefficients of the inverse matrix $F^{-1}$, which depend only on the values of the frequencies used, are calculated beforehand. The method therefore reduces to the calculation of a series of multiplications.

Thus, for example for measurement frequencies of 0.300, 1 and 3 MHz, the numerical values of the different elements of the tables are the following:

$$\begin{bmatrix} a0 \\ a1 \\ a2 \end{bmatrix} = \begin{bmatrix} 1.5873 & -0.6429 & 0.0556 \\ -2.1164 & 2.3571 & -0.2407 \\ 0.5291 & -0.7143 & 0.1852 \end{bmatrix} \times \begin{bmatrix} Cx(f5) \\ Cx(f6) \\ Cx(f7) \end{bmatrix} \text{In}$$

order to improve the robustness of the method, a larger number of measurements can be carried out, at additional frequencies. A similar method is then used, in which the inverse matrix is replaced by a so-called "pseudo-inverse" matrix the coefficients of which are also pre-calculated.

The dispersion is observed by changing variable z=Ln f, i.e. $f=e^z$.

$$Cx = a0 + a1 e^z + a2 e^{2z} + a3 e^{3z} + \ldots + an\, e^{nz}$$

The characteristic frequency fc is found by seeking the position of the inflexion point.
This results in:

$$dCx/dz = a_0 + a_1 e^z + a_2 e^{2z} + a_3 e^{3z} + \ldots + a_n e^{nz}$$

$$d^2Cx/dz^2 = a1 e^z + 4a2 e^{2z} + 9a3 e^{3z} + \ldots + n^2 an\, e^{nz}$$

The point of inflexion is found when the second differential is zero, which leads to:

$$d^2Cx/dz^2 = 0 = a1 + 4a2 e^z + 9a3 e^{2z} + \ldots + n^2 an\, e^{(n-1)z}$$

By carrying out the inverse change of variables, the following is obtained:

$$0 = a1 + 4a2fc + 9a3fc^2 + \ldots + n^2 an\, fc^{(n-1)}$$

For a polynomial P(f) of degree 2, the relationship reduces to:

$$0 = a1 + 4a2fc, \text{ i.e. } fc = -a1/(4a2)$$

It is essential for the concavity of the polynomial of degree 2 to be oriented downwards, i.e. the coefficient a2 is positive. In the opposite case, the frequency corresponding to the point of inflexion is negative, i.e. the characteristic frequency is in fact too high with respect to the range of frequencies measured for a parabola to be fitted to the measurements.

Alternatively, a polynomial P(f) of degree 3 can be used. The calculation is scarcely more involved: the following are obtained by differentiation $$0 = a1 + 4a2fc + 9a3fc^2, \text{ equation of the second degree}$$

which leads to $$\Delta' = 4a2^2 - 9a1a3, \text{ resulting in}$$

$$fc = [-2a2 \pm (4a2^2 - 9a1a3)^{1/2}]/(9a3)$$

On the other hand, for polynomials of a higher degree, it would be necessary to carry out a numerical resolution, for example by using the Newton-Raphson method. This would then pose the problem of identification of the relevant solution.

The search for the position of the point of inflexion is based on an iterative process such as $fi+1 = fi - Pi/P'i$ The polynomial is therefore differentiated once again, obtaining $$P'i = 4a2 + 18a3fc + \ldots + (n-1)n^2 an\, fc^{(n-2)}$$

For a polynomial of degree 3, the iteration formula reduces to:

$$fi+1 = fi - Pi/P'i = fi - (a1 + 4a2fi + 9a3fi^2)/(4a2 + 18a3fi)$$

The solution is generally arrived at with acceptable precision in three iterations. The main problem is to determine initial conditions sufficiently close to the solution to be converged upon. It is then possible to start from the lowest measurement frequency used fmin (0.3 MHz), but in certain cases (high fc), the algorithm then converges towards a point of inflexion situated at fc<0. It is then necessary to repeat the iteration starting with the highest frequency value used fmax.

The coefficient a of the dielectric medium, is obtained by calculating the gradient of the dispersion curve in the vicinity of the characteristic frequency fc. From the Cole-Cole relationship, the gradient at the point of inflexion is given by the relationship:

$$(dCx/df)_{fc} = -a0(1-\beta)/(2fc(1+\sin(p \cdot a/2)))$$

This relationship is not nonsingular, i.e. it is not possible to obtain a value of a analytically. In order to arrive at this, another approach involves showing that the dispersion function as a function of the frequency established empirically by Cole and Cole can be advantageously replaced by the function:

$$Cx = Cx_{high} + \Delta Cx/(1 + (f/fc)^{2(1-b)})$$

in which the coefficient $\beta$ is comprised between 0 and 1. This new relationship is not intrinsically better or less good than that of Cole and Cole, since it is also empirical. It is not however possible to discern one relationship from the other experimentally. This new relationship allows the analytical calculation of the coefficient $\beta$.

The following relationship in fact results:

$$(dCx/df)_{fc} = -a0(1-\beta)/(2fc) = a1 + 2a2fc + 3a3fc^2 + \ldots + n\, an\, fc^{(n-1)}$$

which leads to $\beta$:

$$\beta 1 + 2fc(a1 + 2a2fc + 3a3fc^2 + \ldots + n\, an\, fc^{(n-1)})/a0$$

An empirical relationship makes it possible, if necessary, to recalculate the value of the coefficient a from that of $\beta$. The following approximate relationship has in fact been easily established:

$$a(0.627314\, \beta^2 - 0.061700\, \beta + 0.439407)\, \beta$$

an expression which, for values of a comprised between 0 and 0.5, the usual variation range, can be refined to $$a = (0.495698\beta^2 - 0.062162\beta + 0.413456)\beta$$

Alternatively, because of the symmetrical character of the $\beta$ dispersion around the point of inflexion corresponding to the characteristic frequency fc, it is possible to use the highest frequencies, always including the frequency fc. A change in variables must then be carried out, by positing h=1/f and ne=1/fc. The mathematical processing is then carried out as explained previously, but leads to Cfhigh, by extrapolating the polynomial used to h=0. fc is obtained by inverting the value of hc found.

This variant is particularly useful because the errors associated with the systematic and random polarizations only slightly affect the capacitance measurements carried out at high frequencies. Moreover, it is found experimentally that the measurement noise is also further reduced, which makes it possible to obtain values of the descriptors which are also less noisy.

The value of the three descriptors characterizing the $\beta$ dispersion is thus obtained. It is now possible to use this information in order to improve the biomass measurement. In fact, we have seen that the capacitance measurement returned a value proportional to the product $P \cdot r \cdot Cm$, which is therefore dependent on the size of the cells. We have also seen that the value of fc is inversely proportional to the product $r \cdot Cm$. By finding the product $C \cdot fc$, the unknown variables r and Cm are therefore eliminated, and a value independent of the membrane capacitance and especially of size is obtained, which can vary greatly. The following is obtained:

$$p = \frac{2}{9}\Delta\varepsilon \cdot f_c \pi \frac{1}{\sigma_c} + \frac{1}{2\sigma_m}$$

In this expression, the volume fraction of biomass P no longer depends only on a single unknown variable s c, since s m can be measured by the biomass measurement device at the same time as the capacitance. As s c is a variable which is metabolically regulated, and it a been experimentally shown that it was remarkably insensitive to variations in the conductivity s m of the medium, it is thus possible to arrive at an evaluation of the volume fraction P which is clearly improved compared with the simple measurement of the dielectric increment.

Of course the invention is not limited to the examples which have just been described and numerous changes can be made to these examples without exceeding the scope of the invention. In particular, the determination method according to the invention can be implemented in biomass measurement devices other than that described in the document FR2812725.

The invention claimed is:

1. A method for determining biomass in a dielectric medium, in particular a medium comprising cells in suspension in a fluid, comprising:
    obtaining the biomass (X) from capacitance and conductance measurements that are carried out with a device comprising electrodes and electronic means for processing the capacitance and conductance signals obtained from said electrodes, the biomass (X) being determined from a difference ($\Delta C_x(G,f_2)$) between:
    a first capacitance signal ($C_{X\_FG\_C}(G,f_2)$) of said medium, measured at a first frequency ($f_2$) and corrected according to at least one level of correction, this first level of correction comprising a step of correcting said first measured signal ($Cm\_(G, f_2)$) according to a model ($Ccal(G, f_2)$) dependent on the conductance of the medium at said first frequency ($f_2$), and
    a second capacitance signal ($Cm\_cor(G,f_3)$) of said medium, measured at a second frequency ($f_3$) and corrected according to the at least one level of correction, this first level of correction comprising a step of correcting said second measured signal ($Cm\_(G, f_3)$) according to a model ($Ccal(G, f_3)$) dependent on the conductance of the medium at said second frequency ($f_3$),
    wherein each of the measured signals is separately corrected according to the at least one level of correction.

2. The method according to claim 1, further comprising:
    a second level of correction comprising correcting said first and second corrected capacitance signals, from a third capacitance measurement ($Cm\_(G, f_1)$) carried out at a third frequency ($f_1$), itself corrected by a conductance measurement ($Ccal(G, f_1)$) carried out at said third frequency.

3. The method according to claim 2, implemented for a medium comprising cells in suspension in a medium, wherein the method further comprises a third level of correction using a model of the behaviour of a β dispersion in said medium.

4. The method according to claim 1, the capacitance signal being contaminated with capacitance errors due to random polarization, capacitance errors due to systematic polarization, and capacitance errors due to the overall errors originating from the electronic means, wherein the capacitance errors due to random polarization are corrected separately from those due to systematic polarization and those due to the electronics, and in that the method also comprises:
    global modelling of the systematic polarization and of the capacitance errors due to the overall errors of the electronics, in the form of a common equation $C_{cal}(G,f)$, a function of the conductance G of the medium and the excitation frequency f of the conductive electrodes, and
    determining a corrected capacitance value $Cm\_cor(G, f)$, by comparing each raw capacitance measurement $Cm(G, f)$ originating from the device and carried out at a predetermined frequency, to the value of said common equation of the model $C_{cal}(G,f)$ at said predetermined frequency.

5. The method according to claim 4, wherein the common equation of the model $C_{cal}(G, i)$ is of polynomial form, or can be approximated by a polynomial form.

6. The method according to claim 4, wherein the common equation of the model $C_{cal}(G, f)$ of polynomial form is of order 3 or 4.

7. The method according to claim 4, wherein the common equation of the model $C_{cal}(G, f)$ has coefficients calculated for a plurality of predetermined frequencies used by the device.

8. The method according to claim 4, wherein the capacitance errors corrected by the common equation of the model $C_{cal}(G, f)$ comprise capacitive errors as a function of conductance and frequency.

9. The method according to claim 8, wherein coefficients of the correction model $C_{cal}(G, f)$ are determined from a calibration operation in a reference medium containing no biological cells and the conductance of which is modified so as to cover the full scale of the conductance range of the device.

10. The method according to claim 4, wherein the capacitance errors corrected by the common equation of the model $C_{cal}(G, f)$ include errors linked to line effects.

11. The method according to claim 4, wherein the capacitance errors corrected by the common equation of the model $C_{cal}(G, f)$ include errors linked to imperfections in the sensor.

12. The method according to claim 4, wherein the correction model of common equation $C_{cal}(G, f)$ eliminates uncertainty regarding the systematic polarization development gradient as a function of the excitation frequency.

13. The method according to claim 4, wherein the correction model of common equation $C_{cal}(G, f)$ eliminates a product of a combined effect of aeration of the medium and overall errors of electronics within the device.

14. The method according to claim 4, wherein the determination of the capacitance error due to random polarization is carried out at a predetermined frequency $f_1$ chosen to be 100 kHz.

15. The method according to claim 14, wherein the random polarization capacitance $Cm\_cor(G, f_1)$ is calculated at the frequency $f_1$ by comparison between the raw capacitance measurement originating from the device and the correction model $Ccal(G, f_1)$.

16. The method according to claim 14, wherein the method further comprises determining the capacitance of the dielectric medium at a second predetermined frequency $f_2$.

17. The method according to claim 16, implemented for a measurement carried out on a biological cell suspension, wherein the second predetermined frequency $f_2$ is chosen close to the characteristic frequency fc of said suspension, characteristic of the β dispersion of the cells in suspension.

18. The method according to claim 16, wherein the capacitance of the dielectric medium $Cm\_cor(G, f_2)$ is calculated at the frequency $f_2$, by comparison between the raw capacitance measurement originating from the device and the conductance model $Ccal(G, f_2)$.

19. The method according to claim 14, wherein the determination of the capacitance of the dielectric medium implements a correction model resulting from a combination:
    of the random polarization capacitance measurement $Cm\_cor(G, f_1)$, estimated at the first predetermined frequency $f_1$,
    of the capacitance measurement of the medium $Cm\_cor(G, f_2)$, estimated at the second predetermined frequency $f_2$, and of the behaviour model of the random polarization $a_{alea} \cdot f^p \cdot G^2$.

20. The method according to claim 19, implemented for the measurement of biological cell suspensions according to a behaviour model of the type
    $\Delta$ capacitance $Cx(G, f) = \Delta C_{cell} \times 1/(1+(f/f_c)^2)$ where $f_c$ is the characteristic frequency of the medium.

21. The method according to claim 20, wherein the characteristic frequency $f_c$ is predetermined from a calculation chart.

22. The method according to claim 20, wherein the characteristic frequency $f_c$ is determined in line by a method for the determination of characteristic parameters of a β dispersion.

23. The method according to claim 20, wherein the dielectric measured at the first predetermined frequency $f_1$ is substantially identical to the dielectric measured at the second predetermined frequency $f_2$.

24. The method according to claim 20, implemented for the measurement of a medium containing biological cells, wherein the method further comprises determining a capacitance error $Cm\_cor(G, f_3)$ due to thermal drift of an offset of the electronics and to variations in the capacitance of the dielectric suspension medium, at a third predetermined frequency $f_3$.

25. The method according to claim 24, wherein the capacitance error $Cm\_cor(G, f_3)$ is calculated at the third predetermined frequency $f_3$, by comparison between the raw capacitance measurement originating from the device and the correction model $Ccal(G, f_3)$.

26. The method according to claim 25, wherein the method further comprises correcting raw or corrected capacitance measurements, contaminated with errors due to the thermal drift of the offset of the electronics and to variations in capacitance of the suspension medium, by subtracting from these measurements the capacitance error $Cm\_cor(G, f_3)$.

27. The method according to claim 1, wherein the method further comprises a modelling of the random polarization according to a behaviour model such as $a_{alea} \cdot f^p \cdot G^2$, in which:
G is the conductance of the medium,
$a_{alea}$ is a predefined constant, and
p is the polarization gradient.

28. The method according to claim 1, wherein the method further comprises converting the capacitance and conductance values of the medium to permittivity and conductivity values, by multiplication of said capacitance and conductance values by a probe factor k.

29. The method according to claim 28, wherein the method further comprises determining the probe factor k, from division of the conductivity value of a liquid solution of known conductivity by a conductance measurement value of said solution.

30. The method according to claim 28, wherein the method further comprises determining a probe factor $k_a$ linked to the aeration of the medium, at a fourth predetermined frequency $f_4$.

31. The method according to claim 30, wherein the fourth predetermined frequency is chosen such that the dielectric is the most stable whatever the changes in environmental parameters.

32. The method according to claim 30, wherein the probe factor $k_a$ represents an apparent geometric modification of the sensor when bubbles are present in the dielectric medium.

33. The method according to claim 30, wherein the method further comprises determining the capacitance $Cm\_cor(G, f_4)$ linked to the factor $k_a$ at the frequency $f_4$ by comparison of the raw capacitance measurement with the conductance model $Ccal(G, f_4)$.

34. The method according to claim 33, wherein the probe factor $k_a$ is for example calculated by relating the capacitance $Cm\_cor(G, f_4)$ to a capacitance value of a non-aerated reference medium.

35. The method according to claim 30, wherein the probe factor $k_a$ is used in order to determine the corrected permittivity of the dielectric medium from the effects of aeration on the capacitance measurement, and in order to determine the conductivity of the medium by correcting the effects of aeration on the conductance measurement.

36. The method according to claim 30, wherein the method further comprises determining parameters characteristic of a dielectric dispersion on media containing biological cells, by using at least three predetermined frequencies $f_5, f_6, f_7$.

37. The method according to claim 36, wherein the method further comprises determining capacitances linked to the dispersion $Cm\_cor(G, f_5), Cm\_cor(G, f_6), Cm\_cor(G, f_7)$, at the at least three predetermined frequencies $f_5, f_6, f_7$, by comparing raw capacitance measurements originating from the device to the conductance models at the corresponding frequencies $Ccal(G, f_5), Ccal(G, f_6)$, and $Ccal(G, f_7)$.

38. The method according to claim 36, wherein the method further comprises determining the characteristic parameters of the dielectric dispersion, comprising:
measuring a number n of corrected measured capacitance values $Cm\_cor(G, f_{5\ to\ m})$ with $m=5+n-1$, at n frequencies distributed over the frequency range corresponding to that of the dielectric dispersion studied, n being greater than or equal to 3,
adjusting a multilinear function dependent on frequency and comprising n variable coefficients in order best to approach the n values of measured corrected capacitance, and
calculating the parameters characteristic of the dielectric dispersion from the coefficients of the multilinear function.

39. The method according to claim 38, wherein the multilinear function dependent on the frequency is constituted by a polynomial of degree $n-1$.

40. The method according to claim 39, wherein the method further comprises calculating an evaluation of the concentration of biomass of the medium, from the values of the coefficients of the polynomial of degree $n-1$.

41. The method according to claim 39, wherein the method further comprises calculating the evaluation of the size of the microorganisms in the medium, from the coefficients of the polynomial of degree $n-1$.

42. The method according to claim 1, wherein the method further comprises determining the concentration of biomass of the medium, by multiplying the permittivity variation measured at the second predetermined frequency $f_2$ by a predetermined coefficient Y.

43. The method according to claim 42, wherein the method further comprises determining the predetermined coefficient Y using a calculation chart of physical parameters characteristic of biological cells.

44. The method according to claim 42, wherein the method further comprises determining the predetermined coefficient Y using a previous calibration in a biomass suspension medium the concentration of which is known.

45. A device for determining a biomass in a dielectric medium to be measured, in particular a medium comprising cells in suspension in a fluid, from a difference $(\Delta C_x(G,f_2))$ between:
a first capacitance signal $(C_{X\_FG\_C}(G,f_2))$ of said medium, measured at a first frequency $(f_2)$ and corrected according to at least one level of correction, this first level of correction comprising a step of correcting said first measured signal $(Cm\_(G, f_2))$ according to a model $(Ccal(G, f_2))$ dependent on the conductance of the medium at said first frequency $(f_2)$, and
a second capacitance signal $(Cm\_cor(G,f_3))$ of said medium, measured at a second frequency $(f_3)$ and corrected according to the at least one level of correction, this first level of correction comprising a step of correcting said second measured signal $(Cm\_(G, f_3))$ according to a model $(Ccal(G, f_3))$ dependent on the conductance of the medium at said second frequency$(f_3)$, said device implementing the method according to claim 1, and comprising means for correcting a capacitance signal originating from a device generating a capacitance and conductance signal, this device being linked to a sensor having conductive electrodes in direct contact with the dielectric medium to be measured, this capacitance signal being contaminated with capacitance errors due to random polarization and capacitance errors due to systematic polarization, wherein the means of correction of the capacitance signal are arranged in order to separately correct on the one hand the capacitance errors due to random polarization and on the other hand the errors due to systematic polarization, and comprise:

means for modelling systematic polarization and capacitance errors including errors due to systematic polarization, in the form of a common equation $C_{cal}(G, f)$, a function of the conductance of the medium and excitation frequency of the conductive electrodes, this equation being arranged in order to eliminate the product of the combined effect of polarization and of the overall errors of the electronics within the device, and means for determining a corrected capacitance value Cm_cor(G, f), by comparing each raw capacitance measurement Cx(G, f) originating from the device and carried out at a predetermined frequency, with the value of said common equation of the model $C_{cal}(G, f)$ at said predetermined frequency.

46. The device according to claim 45, further comprising means for determining the capacitance error due to random polarization at a first predetermined frequency $f_1$ chosen to be 100 kHz.

47. The device according to claim 46, further comprising means for determining the capacitance of the dielectric medium at a second predetermined frequency $f_2$ chosen to be close to the characteristic frequency fc of the medium, characteristic of the β dispersion of the cells in suspension.

48. The device according to claim 47, wherein the means for determining the capacitance of the dielectric medium implement a correction model resulting from a combination:
- of a capacitance measurement of random polarization Cm_cor(G, $f_1$), estimated at the first predetermined frequency $f_1$,
- of a capacitance measurement of the medium Cm_cor(G, $f_2$), estimated at the second predetermined frequency $f_2$,
- and of a behaviour model of random polarization $a_{alea} \cdot f^p \cdot G^2$, in which G is the conductance of the medium, $a_{alea}$ is a predefined constant, and p is the polarization gradient.

49. The device according to claim 48, implemented for measuring a medium containing biological cells, wherein the device further comprises means for determining a capacitance error Cm_cor(G, $f_3$) due to the thermal drift of the offset of the electronics and to variations in the capacitance of the dielectric suspension medium, at a third predetermined frequency $f_3$.

50. The device according to claim 49, further comprising means for determining a capacitance Cm_cor(G, $f_4$) linked to a probe factor $k_a$ linked to the aeration of the medium, at a fourth predetermined frequency $f_4$.

51. The device according to claim 50, further comprising means for determining parameters characteristic of a dielectric dispersion on media containing biological cells, by using at least three predetermined frequencies $f_5$, $f_6$, $f_7$.

52. The device according to claim 45, further comprising means for determining parameters characteristic of the dielectric dispersion, comprising:

means for measuring a number n of corrected capacitance values Cm_cor(G, $f_{5\ to\ m}$) with m=5+n−1, at n frequencies distributed over the frequency range corresponding to that of the dielectric dispersion studied, n being greater than or equal to 3, means for adjusting a multilinear function dependent on frequency and comprising n variable coefficients for best approaching the n measured corrected capacitance values, and means for calculating parameters characteristic of the dielectric dispersion from the coefficients of the multilinear function.

53. An impedance measurement apparatus, arranged for providing a measurement of the real part of an impedance and of the capacitance corresponding to this impedance, the apparatus including a device for determining a biomass of a biological dielectric medium to be measured according to claim 45, comprising means for correcting said capacitance measurement, this capacitance measurement being contaminated with capacitance errors due to a random polarization and capacitance errors due to a systematic polarization, said means for correcting the capacitance signal being arranged in order to separately correct on the other hand the capacitance errors due to random polarization and on the other hand the errors due to systematic polarization, and comprising:

means for modelling the systematic polarization and capacitance errors including errors due to the systematic polarization, in the form of a common equation $C_{cal}(G, f)$, a function of the conductance of the medium and the excitation frequency of the conductive electrodes, this equation being arranged in order to eliminate the product of the combined effect of the polarization and the overall errors of the measurement electronics, and, means for determining a corrected capacitance value Cm_cor(G, f), by comparing each raw capacitance measurement Cx(G, f) carried out at a predetermined frequency, with the value of said common equation of the model $C_{cal}(G,f)$ at said predetermined frequency.

54. An apparatus for measuring a biomass of a biological dielectric medium to be measured, implementing a method for biomass determination according to claim 1, provided for generating a capacitance signal and a conductance signal, comprising measurement electronics linked to a sensor provided with conductive electrodes in direct contact with the medium to be measured, characterized in that it includes a device for biomass determination comprising means for correcting said capacitance signal, this capacitance signal being contaminated with capacitance errors due to random polarization and capacitance errors due to systematic polarization, said means for correcting the capacitance signal being arranged for separately correcting on the other hand the capacitance errors due to random polarization and on the other hand the errors due to systematic polarization, and comprising:

means for modelling the systematic polarization and capacitance errors including errors due to systematic polarization, in the form of a common equation $C_{cal}(G, f)$, a function of the conductance of the medium and the excitation frequency of the conductive electrodes, this equation being arranged in order to eliminate the product of the combined effect of the polarization and the overall errors of the measurement electronics, and means for determining a corrected capacitance value $Cm\_cor(G, f)$, by comparing each raw capacitance measurement $Cx(G, f)$ carried out at a predetermined frequency, with the value of said common equation of the model $C_{cal}(G,f)$ at said predetermined frequency.

55. The method according to claim 1, wherein obtaining the biomass comprises evaluating a concentration (X) of biomass of the medium.

56. The method according to claim 1, wherein obtaining the biomass comprises evaluating a size of microorganisms in the medium.

57. The method according to claim 1, wherein obtaining the biomass comprises evaluating a volume fraction (P) of the biomass in the medium.

* * * * *